US009816878B2

(12) United States Patent
Uno et al.

(10) Patent No.: US 9,816,878 B2
(45) Date of Patent: Nov. 14, 2017

(54) TEMPERATURE MEASUREMENT SYSTEM AND ABNORMALITY DETECTION METHOD

(71) Applicant: FUJITSU LIMITED, Kawasaki-shi, Kanagawa (JP)

(72) Inventors: Kazushi Uno, Atsugi (JP); Fumio Takei, Isehara (JP); Takeo Kasajima, Machida (JP); Kyoko Tadaki, Atsugi (JP); Minoru Ishinabe, Atsugi (JP)

(73) Assignee: FUJITSU LIMITED, Kawasaki (JP)

( * ) Notice: Subject to any disclaimer, the term of this patent is extended or adjusted under 35 U.S.C. 154(b) by 289 days.

(21) Appl. No.: 14/695,615

(22) Filed: Apr. 24, 2015

(65) Prior Publication Data

US 2015/0233771 A1    Aug. 20, 2015

Related U.S. Application Data

(63) Continuation of application No. PCT/JP2012/077782, filed on Oct. 26, 2012.

(51) Int. Cl.
*G01K 11/32* (2006.01)
*G01N 25/72* (2006.01)

(52) U.S. Cl.
CPC ......... *G01K 11/3206* (2013.01); *G01N 25/72* (2013.01); *G01K 2011/324* (2013.01)

(58) Field of Classification Search
CPC ......... G01K 11/3206; G01K 2011/324; G01N 25/72; H02M 1/32; H02M 1/38;
(Continued)

(56) References Cited

U.S. PATENT DOCUMENTS 5,308,162 A * 5/1994 Amano ............... G01M 3/047
                                               374/131
6,547,435 B1    4/2003 Grosswig et al.
(Continued)

FOREIGN PATENT DOCUMENTS

JP    2-201133    8/1990
JP    3-285129    12/1991
(Continued)

OTHER PUBLICATIONS

Chinese Office Action dated Jun. 17, 2016 in corresponding Chinese Patent Application No. 201280076614.7.
(Continued)

*Primary Examiner* — Manish S Shah
(74) *Attorney, Agent, or Firm* — Staas & Halsey LLP

(57) ABSTRACT

A temperature measurement system includes an optical fiber, a temperature distribution measurement apparatus, and a data processing apparatus. The temperature distribution measurement apparatus is configured to detect backscattered light by causing light to enter the optical fiber, and acquire the temperature distribution of the optical fiber in the length direction thereof based on the result of the detection. The data processing apparatus is configured to store therein the temperature distribution acquired by the temperature distribution measurement apparatus, perform signal processing on a difference temperature distribution obtained by computing the difference between a current temperature distribution and a past temperature distribution, and determine whether or not abnormality is present based on the result of the signal processing.

18 Claims, 16 Drawing Sheets

(58) Field of Classification Search
CPC ........... H02M 1/53806; H03K 17/0822; G01R 31/2642; G01R 31/048; G01R 31/40
See application file for complete search history.

(56) References Cited

U.S. PATENT DOCUMENTS

| | | |
|---|---|---|
| 2012/0033709 A1 | 2/2012 | Kasajima et al. |
| 2013/0215930 A1 | 8/2013 | Kasajima et al. |

FOREIGN PATENT DOCUMENTS

| | | | |
|---|---|---|---|
| JP | 7-243920 | 9/1995 | |
| JP | 8-106586 | 4/1996 | |
| JP | 11-118742 | 4/1999 | |
| JP | 2962452 | 10/1999 | |
| JP | 2962452 B2 * | 10/1999 | ........... F25J 3/04763 |
| JP | 2002-515597 | 5/2002 | |
| JP | 2009-265083 | 11/2009 | |
| JP | 2011-232138 | 11/2011 | |
| WO | WO 99-060360 | 11/1999 | |
| WO | WO 2010/125712 A1 | 11/2010 | |
| WO | WO 2012/056567 A1 | 5/2012 | |

OTHER PUBLICATIONS

Canadian Office Action dated Apr. 27, 2016 in corresponding Canadian Patent Application No. 2,889,157.
Australian Office Action dated Feb. 24, 2016 in corresponding Australian Patent Application No. 2012393096.
Extended European Search Report dated Sep. 15, 2015 in corresponding European Patent Application No. 12887214.0.
International Search Report mailed on Dec. 4, 2012 in corresponding International Patent Application No. PCT/JP2012/077782.
Written Opinion of the International Searching Authority mailed Dec. 4, 2012 in corresponding International Patent Application No. PCT/JP2012/077782.
Japanese Office Action dated Apr. 5, 2016 in corresponding Japanese Patent Application No. 2014-543112.

* cited by examiner

TEMPERATURE MEASUREMENT SYSTEM AND ABNORMALITY DETECTION METHOD

CROSS-REFERENCE TO RELATED APPLICATION

This application is a continuation of International Patent Application No. PCT/JP2012/077782 filed on Oct. 26, 2012 and designated the U.S., the entire contents of which are incorporated herein by reference.

FIELD

The embodiments discussed herein are related to a temperature measurement system and an abnormality detection method.

BACKGROUND

In facilities such as chemical plants, oil refinery plants, and thermal power plants which use large amounts of flammable, explosive, or hazardous materials, it is important to detect corrosion and thinning on pipes and tanks at early stages to prevent serious accidents.

To do so, a temperature distribution measurement apparatus (distributed temperature sensor: DTS) is sometimes employed which is configured to use an optical fiber as a temperature sensor.

For example, an optical fiber is laid around a pipe or tank, and the optical fiber's end is connected to the temperature distribution measurement apparatus. Then, laser is applied into the optical fiber from the temperature distribution measurement apparatus, and Raman scattered light generated inside the optical fiber is detected with the temperature distribution measurement apparatus to acquire the temperature of the pipe or tank, and the presence of abnormality is determined based on the obtained result.

In facilities such as chemical plants, oil refinery plants, and thermal power plants, a delay in abnormality detection may lead to serious accidents. Thus, a system capable of detecting the occurrence of abnormality at an even earlier stage is desired.

Note that the following patent document discloses a technique related to the present application.
Patent Document 1: International Patent Pamphlet No. WO 2010/125712

SUMMARY

According to one aspect of a technique disclosed herein, there is provided a temperature measurement system, including: an optical fiber; a temperature distribution measurement apparatus configured to detect backscattered light by causing light to enter the optical fiber, and acquire a temperature distribution of the optical fiber in a length direction of the optical fiber based on a result of the detection; and a data processing apparatus configured to store the temperature distribution acquired by the temperature distribution measurement apparatus in the data processing apparatus, perform signal processing on a difference temperature distribution obtained by computing a difference between a current temperature distribution and a past temperature distribution, and determine whether or not abnormality is present based on a result of the signal processing.

According another aspect of the disclosed technique, there is provided an abnormality detection method, including: by using a temperature distribution measurement apparatus, acquiring backscattered light by causing light to enter an optical fiber from one end of the optical fiber; and by using a data processing apparatus, storing an intensity distribution of the backscattered light acquired by the temperature distribution measurement apparatus in the data processing apparatus, performing signal processing on a difference temperature distribution obtained by computing a difference between a current temperature distribution and a past temperature distribution, and determining whether or not abnormality is present based on a result of the signal processing.

The object and advantages of the invention will be realized and attained by means of the elements and combinations particularly pointed out in the claims.

It is to be understood that both the foregoing general description and the following detailed description are exemplary and explanatory and are not restrictive of the invention.

DESCRIPTION OF EMBODIMENTS

As a prelude for understanding an embodiment, super-resolution signal processing by a temperature measurement system using an optical fiber as a sensor will be described below by taking temperature distribution measurement in a data center as an example.

Figure 1:
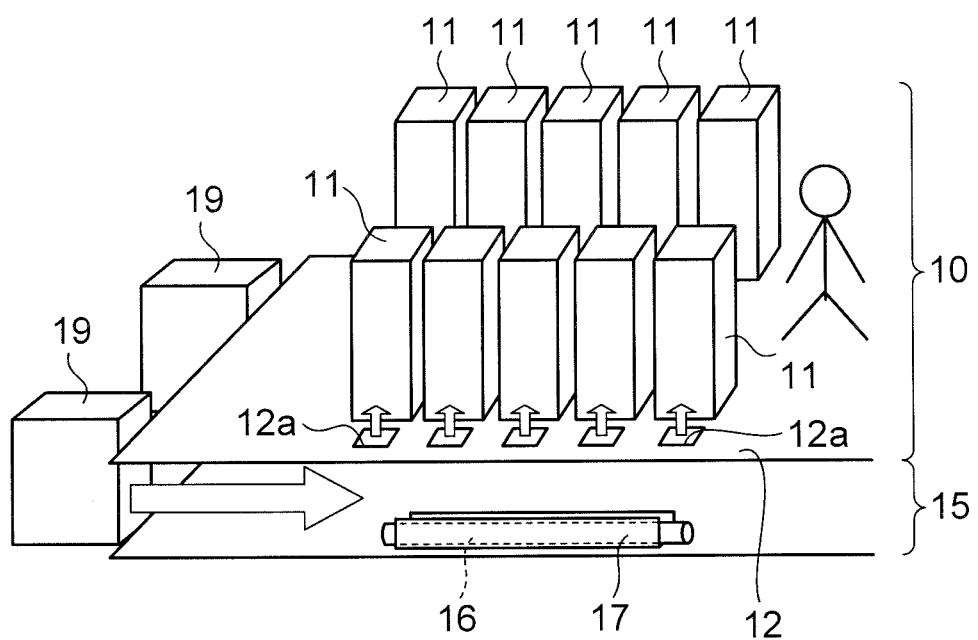
FIG. 1 is a schematic view illustrating the structure of a computer room in a data center.

(Prelude) FIG. 1 is a schematic view illustrating the structure of a computer room in a data center. As illustrated in this FIG. 1, in a general data center, the inside of its computer room is divided into an equipment installation area 10 and a free access floor (underfloor space) 15 provided underneath the equipment installation area 10.

In the equipment installation area 10, many racks 11 housing a plurality of computers (servers) are disposed. Each rack 11 of a general type is configured to use an air blowing fan, which is provided inside the rack 11, to introduce cool air from the front side (air inlet side) of the rack 11, thereby cooling the computers therein, and discharge the air whose temperature has risen due to the cooling from the back or upper side (air outlet side).

In the free access floor 15, various cables 16 such as power cables and communication cables connected to the racks 11 are disposed in a state of being housed in cable ducts 17. Moreover, cool air which is adjusted to given temperatures is supplied to the free access floor 15 from air conditioners 19. The cool air, supplied to the free access floor 15 from the air conditioners 19, is supplied to the equipment installation area 10 through grills 12a provided in a floor 12 of the equipment installation area 10 and taken into each rack 11 from the front side of the rack 11.

For this type of data center, it is desired to measure the temperature distribution in each rack 11 so as to optimize the operation of the air conditioners 11 and reduce the power consumption.

Figure 2:
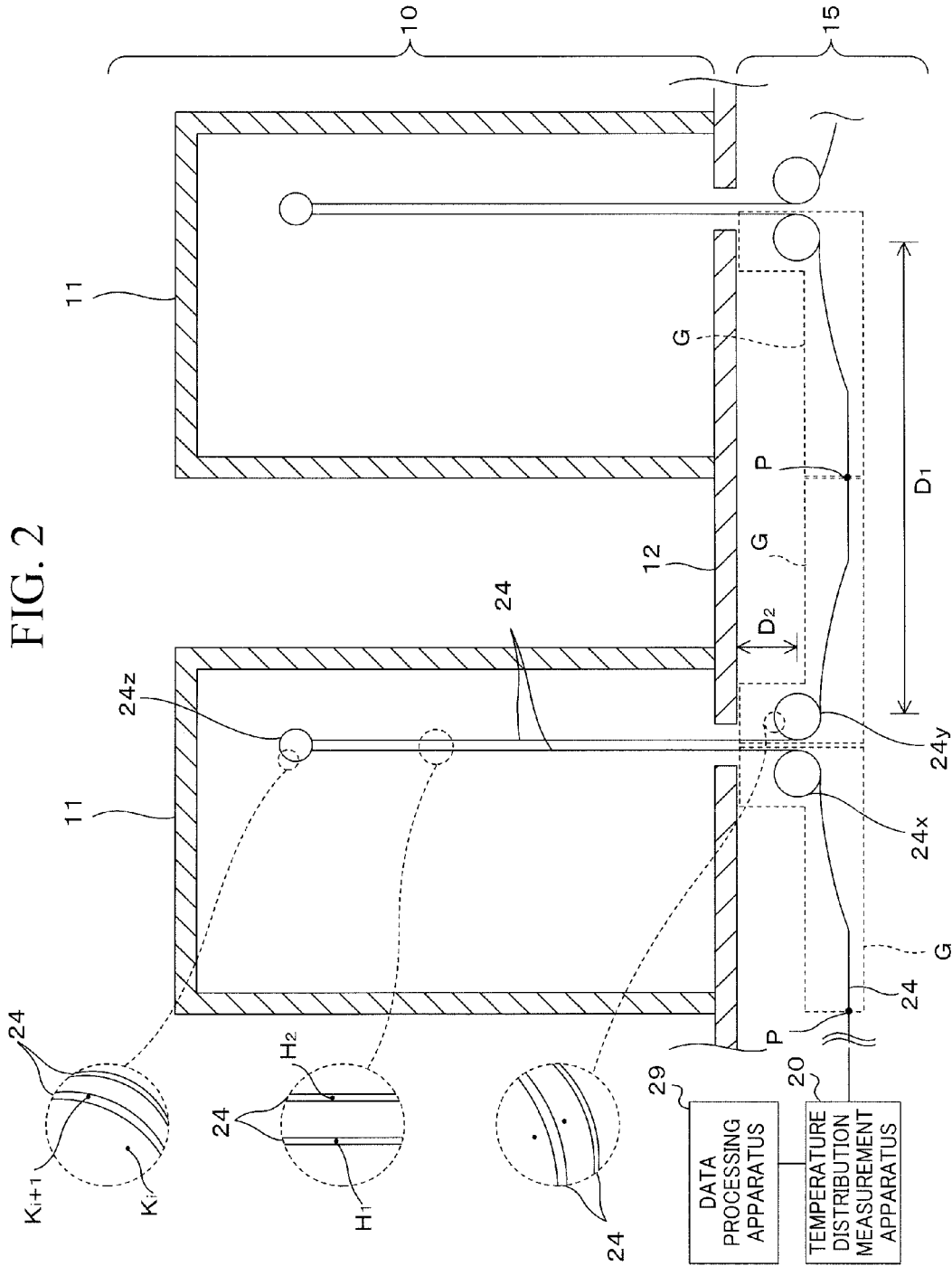
FIG. 2 is a view describing a temperature measurement system using an optical fiber.

FIG. 2 is a view describing a temperature measurement system using an optical fiber.

An end of an optical fiber 24 is connected to a temperature distribution measurement apparatus (DTS) 20. This optical fiber 24 is routed through the free access floor 15, drawn out to the equipment installation area 10 from the free access floor 15, and laid in each rack 11.

In the free access floor 15, winding parts 24x and 24y around each of which the optical fiber 24 is wound by a certain length or longer are provided for each rack 11. The optical fiber 24 between these winding parts 24x and 24y is drawn out to the equipment installation area 10.

The optical fiber 24 drawn to the inside of each rack 11 is laid such that its inwardly extending portion and outwardly extending portion overlap each other at least partially. Moreover, a winding part 24z around which the optical fiber 24 is wound by a certain length or longer is provided at the turning point between the inwardly extending portion and the outwardly extending portion.

The temperature distribution measurement apparatus 20 is configured to output laser of a predetermined pulse width at regular intervals to the optical fiber 24. The temperature distribution measurement apparatus 20 is configured to then detect Raman scattered light (Stokes light and anti-Stokes light) generated in the optical fiber 24 and acquire the temperature distribution of the optical fiber 24 in the length direction based on the result of the detection.

A data processing apparatus 29 is configured to correct data on the temperature distribution outputted from the temperature distribution measurement apparatus 20 by using a transfer function and output the corrected temperature distribution.

Here, the correction of the temperature distribution by the data processing apparatus 29 (super-resolution signal processing) will be described.

Given that a pulse width (ON time) $t_0$ of the laser outputted from the temperature distribution measurement apparatus 20 is 10 nsec, a speed of light c in vacuum is $3 \times 10^8$ m/sec, and a refractive index n of the core of the optical fiber 24 is 1.5, a pulse width W of the laser in the optical fiber 24 is approximately 2 m as described in the equation given below.

$$W = t_0 \cdot c/n = 10 \text{ (nsec)} \cdot 3 \times 10^8 \text{ (m/sec)}/1.5 \approx 2 \text{ (m)}$$

The backscattered light of the laser equivalent to this pulse width is taken into to the temperature distribution measurement apparatus 20 as one signal, and the temperature distribution measurement apparatus 20 detects the temperature from the integrated value of this signal equivalent to the pulse width.

For this reason, the temperature distribution measurement apparatus 20 does not perform accurate temperature measurement without applying heat uniformly to the optical fiber 24 by a length equivalent to the pulse width W. Hereinafter, the length of optical fiber for the temperature distribution measurement apparatus 20 to perform accurate temperature measurement will be referred to as the minimum heating length.

Meanwhile, measurement points are set at regular intervals in the length direction of the optical fiber based on the sampling frequency of the temperature distribution measurement apparatus 20, irrespective of the minimum heating length. The intervals of the measurement points may be 10 cm to several tens of cm in consideration of practical measurement time such as the time for the temperature distribution measurement apparatus 20 to perform averaging.

Figure 3:
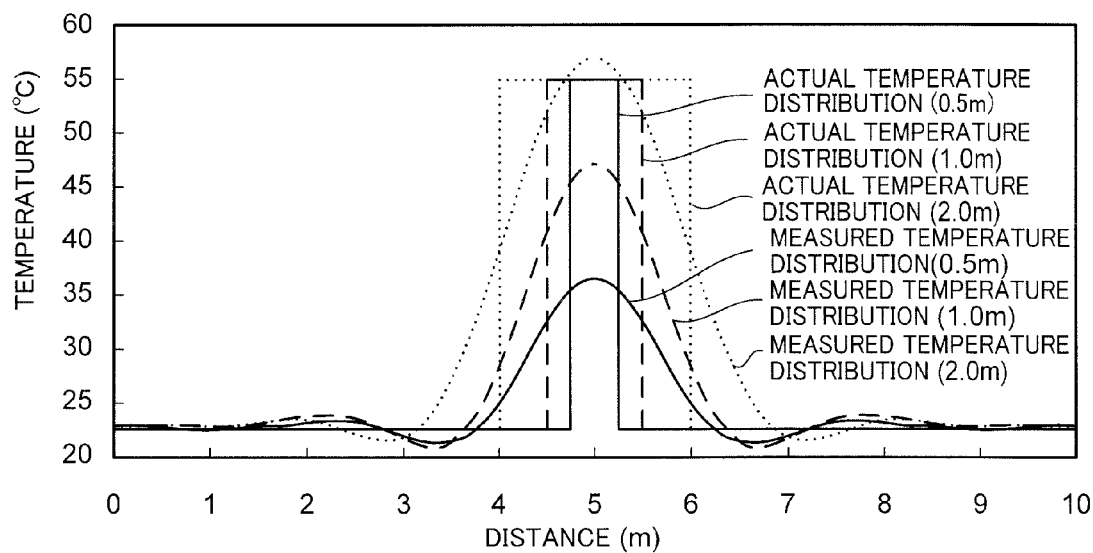
FIG. 3 is a graph illustrating temperature distributions acquired by a temperature distribution measurement apparatus in situations where the optical fiber is disposed in an approximately 23° C. environment and given sections centered at a 5-m location are heated to 55° C.

FIG. 3 is a graph with the horizontal axis representing the distance from the end of the optical fiber versus the vertical axis representing temperature, illustrating temperature distributions acquired by the temperature distribution measurement apparatus in situations where the optical fiber is disposed in an approximately 23° C. environment and given sections centered at a 5-m location are heated to 55° C. Here, the lengths of the sections heated are 0.5 m, 1 m, and 2 m, respectively. Hereinafter, a temperature distribution in a situation where a given section of an optical fiber in the length direction thereof is uniformly heated as described above will be referred to as a stepped temperature distribution.

As is clear from FIG. 3, in the case where a given section of an optical fiber in the length direction thereof is uniformly heated, the resultant temperature distribution obtained by the temperature distribution measurement apparatus (measured temperature distribution) has a shape close to Gaussian distribution (normal distribution). Moreover, the peak of the measured temperature distribution appears lower than the actual temperature in the case where the length of the heated section is shorter than the minimum heating length (2 m), whereas the peak of the measured temperature distribution substantially coincides with the actual temperature in the case where the length of the heated section is equal to or longer than the minimum heating length.

As described above, for the temperature distribution measurement apparatus 20 to accurately measure the temperature, an optical fiber of a length equal to or longer than the minimum heating length needs to be disposed at the same measurement spot.

Moreover, as is clear from FIG. 3, the measured temperature distribution spreads outward from the heated section. For this reason, in the case where there are a plurality of measurement spots, an optical fiber of a certain length or longer is needed between the measurement spots so as to avoid interference therebetween.

Then, if the temperatures at many measurement spots are to be accurately measured, the optical fiber needed will be excessively long, which is not practical.

To solve this, the optical fiber 24 is laid as illustrated in FIG. 2, for example, and the data processing apparatus 29 is caused to correct the temperature distribution acquired by the temperature distribution measurement apparatus 20 (measured temperature distribution) by using a transfer function.

Figure 4:
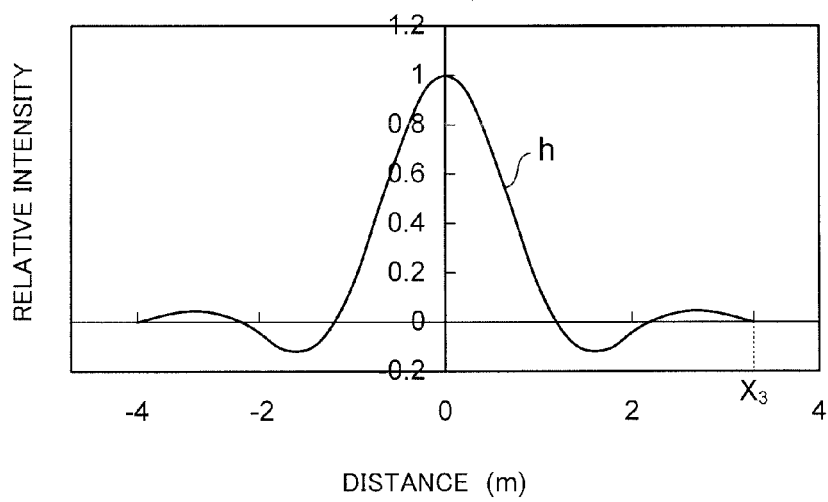
FIG. 4 is a graph illustrating one example of a transfer function.

FIG. 4 is a graph with the horizontal axis representing the distance from the center of a heated section versus the vertical axis representing relative intensity, illustrating one example of the transfer function. A transfer function h is substantially the same as the impulse response characteristics of a measurement system including the optical fiber 24 and the temperature distribution measurement apparatus 20.

The measured temperature distributions in Gaussian curve shapes in FIG. 3 are obtained by convoluting the transfer function h illustrated in FIG. 4 with the stepped temperature distributions in FIG. 3, for example.

The transfer function may be defined as illustrated in FIG. 4, for example, by heating a portion of the optical fiber to a predetermined temperature and measuring the temperature distribution.

The transfer function varies with distance since the optical fiber has group delay characteristics. For this reason, if the optical fiber is equal to or longer than a certain length, it is impossible to define the transfer function uniquely over the entire length. However, even if the optical fiber is long, the optical fiber may be divided into a plurality of sections in the length direction. In this way, the transfer function may be defined under the assumption that loss and delay in optical signal are uniform within a single section. The transfer function not only varies with the distance from the light source but also differs depending on the type of the optical fiber.

Figure 5:
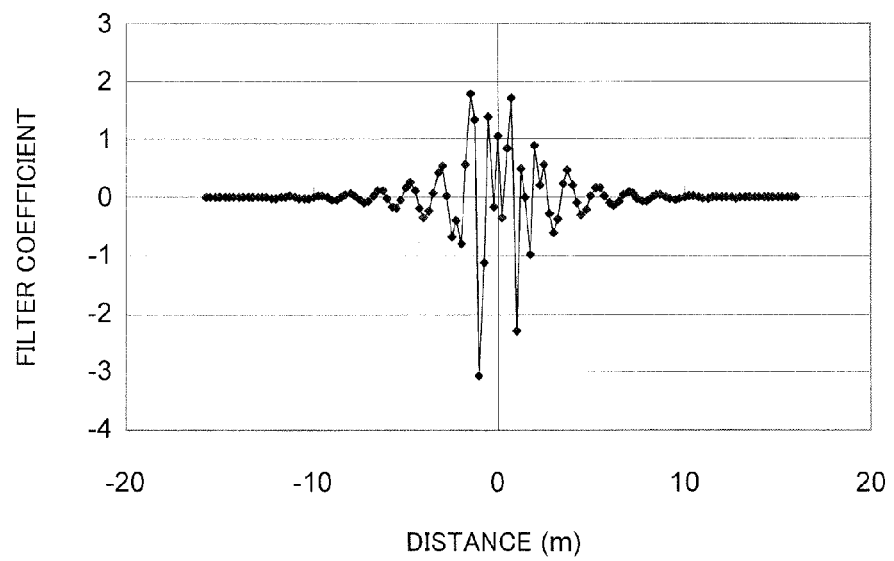
FIG. 5 is a graph illustrating an inverse function of the transfer function in FIG. 4.

FIG. 5 illustrates an inverse function of the transfer function h in FIG. 4. In this FIG. 5, the horizontal axis represents distance and the vertical axis represents coefficient. Hereinafter, the inverse function of the transfer function will be referred to as the inverse filter.

By using the inverse filter to correct (deconvolute) a temperature distribution acquired by the temperature distribution measurement apparatus 20 (measured temperature distribution), a temperature distribution (corrected temperature distribution) closer to the actual temperature distribution is obtained.

Figure 6:
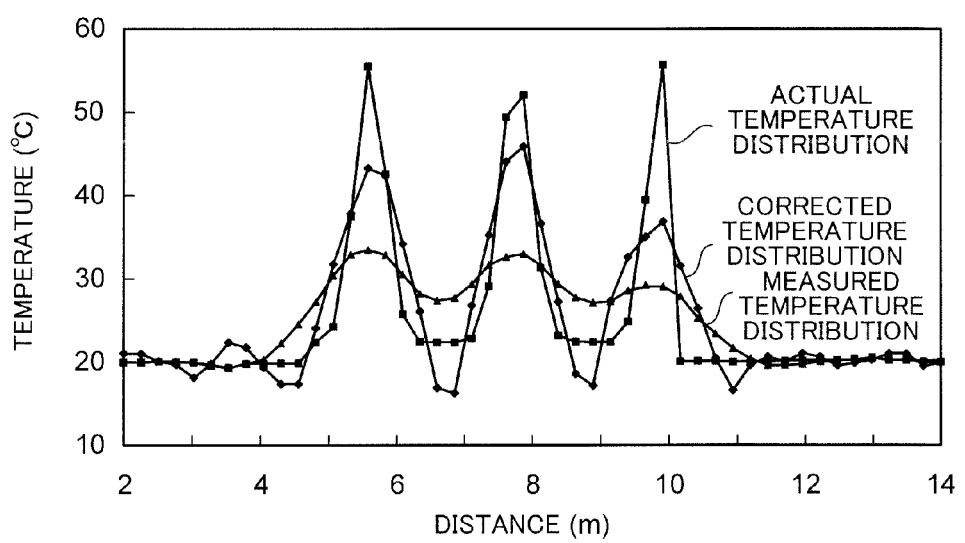
FIG. 6 is a graph illustrating the result of laying an optical fiber in three racks and measuring the temperature distribution of the optical fiber in the length direction thereof with the temperature distribution measurement apparatus.

FIG. 6 is a graph illustrating the result of laying an optical fiber in three racks and measuring the temperature distribution of the optical fiber in the length direction with the temperature distribution measurement apparatus.

FIG. 6 illustrates the temperature distribution obtained by the temperature distribution measurement apparatus (measured temperature distribution), together with a temperature distribution corrected by using the inverse filter (corrected temperature distribution), and the actual temperature distribution. Note that the actual temperature distribution illustrates the result of measurement using a plurality of thermocouples disposed along the path along which the optical fiber is laid.

As is clear from FIG. 6, the measured temperature distribution obtained by the temperature distribution measurement apparatus 20 greatly departs from the actual temperature distribution. The corrected temperature distribution obtained by correcting the measured temperature distribution by using the inverse filter is close to the actual temperature distribution as compared to before the correction. However, this FIG. 6 indicates that it is difficult to well replicate the actual temperature distribution by simply applying the inverse filter to the measured temperature distribution.

The data processing apparatus 29, then, performs a process which brings the corrected temperature distribution closer to the actual temperature distribution by utilizing temperature uniformity to be described below.

As mentioned above, in FIG. 2, the optical fiber 24 is wound around each of the winding parts 24x and 24y by a certain length. Thus, the temperature of the optical fiber 24 at each of the portions wound around the winding parts 24x and 24y may be assumed to be uniform.

For example, in the transfer function illustrated in FIG. 4, a region around the third zero point $X_3$ (=3.3 m) from the origin is convergent to 0, and the measured temperature around this zero point is not influenced by the heat source at the origin.

Then, in the case where a measurement point is at a location away from the equipment installation area 10 by a distance equal to or greater than the distance to the zero point $X_3$ in the length direction of the optical fiber 24, the measured temperature at this measurement point is not influenced by the temperature of the equipment installation area 10 and indicates the actual temperature.

Here, consider a portion of the optical fiber 24 laid in a section G indicated by broken lines in FIG. 2, i.e. a section including a region from the winding part 24x or winding part 24y to the floor 12 and a region from the winding part 24x or winding part 24y to a middle point P between the racks 11. Note that, as illustrated in FIG. 2, the length of the optical fiber 24 between the adjacent racks 11 is $D_1$, and the length of the optical fiber 24 from the winding part 24x or 24y to the floor 12 is $D_2$. Moreover, the temperature of the inside of the free access floor 15 is maintained constant by the cool air supplied from the air conditioners 19.

In this case, a length L of the optical fiber 24 in the section G is equal to $D_1/2 + D_2 D_3$, where $D_3$ is the length which the optical fiber 24 is wound around the winding part 24x or 24y. If this length L is set to be equal to or greater than the distance to the zero point $X_3$ on the transfer function h mentioned above, it means that a measurement point is present in the section G, the measurement point being not influenced by the heat of the computers in the rack 11. In FIG. 2, the middle point P is illustrated as such a measurement point.

The length L is 3.3 m when $D_1$, $D_2$, and $D_3$ are, for example, 1.0 m, 0.5 m, and 2.3 m, respectively. In this way, the length L may be equal to or greater than the distance to the zero point $X_3$ (3.3 m) on the transfer function h.

As mentioned above, the temperature of the inside of the free access floor 15 is uniform. Thus, the temperature at each measurement point on the optical fiber 24 within the section G is the same as the temperature at the middle point P.

The data processing apparatus 29 corrects the measured temperature distribution as described later by utilizing this temperature uniformity within the section G mentioned above.

The example of the laying of the optical fiber 24 illustrated in FIG. 2 has the following feature, in addition the temperature uniformity within the section G mentioned above.

The optical fiber 24 drawn to the inside of the rack 11 is laid such that its inwardly extending portion and outwardly extending portion overlap each other at least partially. Overlapping points $H_1$ and $H_2$ at which the temperature may be assumed to be the same are present at the position where the inwardly extending portion and the outwardly extending portion overlap each other. Then, a condition that the corrected temperatures at the overlapping points $H_1$ and $H_2$ are the same may be added for the correction of the measured temperature distribution.

For a similar reason, the measurement points on the optical fiber 24 on the winding part 24z may also be assumed as overlapping points $K_i$ at which the temperature is substantially the same. Thus, it is possible to add a condition that the corrected temperatures at the overlapping points $K_i$ are the same.

Hereinbelow, a temperature distribution measurement method (super-resolution signal processing) by the temperature measurement system utilizing these features will be described.

Figure 7:
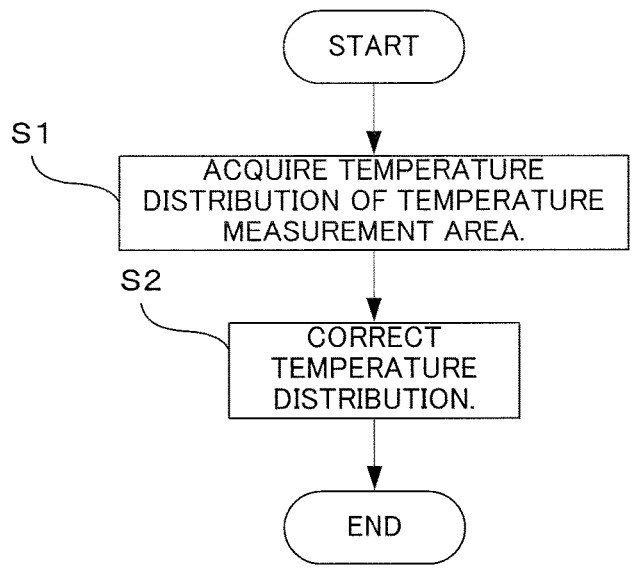
FIG. 7 is a flowchart illustrating a temperature distribution measurement method.

FIG. 7 is a flowchart illustrating the temperature distribution measurement method.

In the first step S1, the temperature distribution measurement apparatus 20 acquires a temperature distribution (measured temperature distribution) along the path along which the optical fiber 24 is laid.

Figure 8:
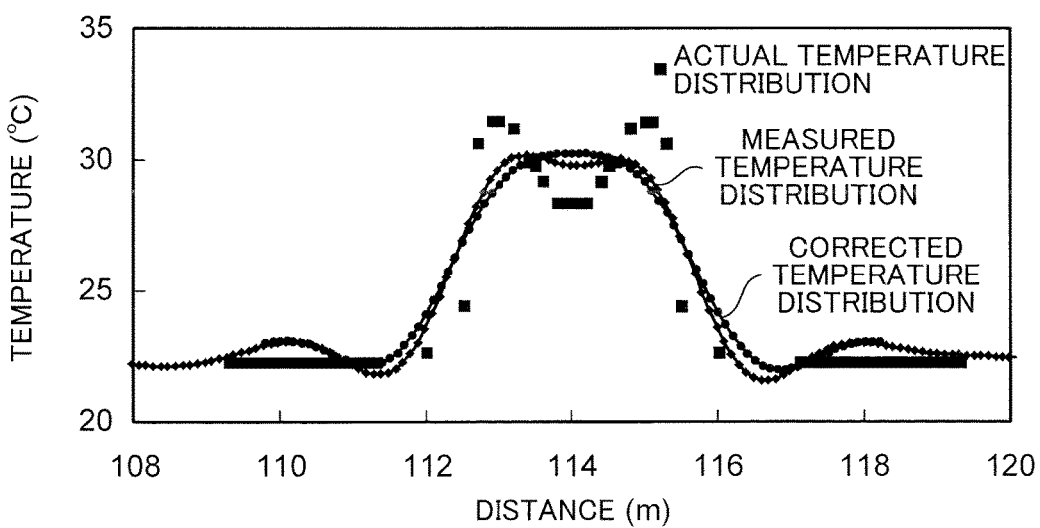
FIG. 8 is a graph illustrating a temperature distribution acquired by the temperature distribution measurement apparatus.

FIG. 8 illustrates the temperature distribution acquired by the temperature distribution measurement apparatus 20, with the horizontal axis representing the distance from the end of the optical fiber 24 versus the vertical axis representing temperature. This FIG. 8 also illustrates the actual temperature distribution measured by using thermocouples and a corrected temperature distribution obtained by the correction using the transfer function.

As is clear from FIG. 8, the measured temperature distribution obtained by the temperature distribution measurement apparatus 20 departs from the actual temperature distribution obtained by the thermocouples.

Thus, in the next step S2, the measured temperature distribution is corrected as follows to be close to the actual temperature distribution.

The measured temperature distribution may be expressed as the equation (1) given below.

[Equation 1]

$$y = \{y_k\}_{k=0}^{k=\infty} \qquad (1)$$

Here, the subscript k of the component $y_k$ represents one of measurement points set along the path along which the optical fiber is laid, and the component $y_k$ is a value obtained by subtracting a measured temperature value in a region where the temperature remains unchanged (a temperature value $T_{AB}$ at the middle point P in the example illustrated in FIG. 2) from a measured temperature value at the measurement point k.

On the other hand, the actual temperature distribution may be expressed as the equation (2) given below.

[Equation 2]

$$x = \{x_i\}_{i=0}^{i=\infty} \qquad (2)$$

Like the equation (1), the subscript i of the component $x_i$ represents a measurement point, and the component $x_i$ is a value obtained by subtracting the measured temperature value in the region where the temperature remains unchanged (the temperature value $T_{AB}$ at the middle point P in the example illustrated in FIG. 2) from the actual temperature at the measurement point i.

The measured temperature distribution y may be expressed as the equation (3) given below as convolution of the actual temperature distribution x and the transfer function h.

[Equation 3]

$$y_k = \sum_{i=0}^{\infty} h_{k-i} x_i \qquad (3)$$

Note that the range of i is such a range that the subscript k-i is equal to or greater than 0.

Moreover, this may be written on a component basis as the equation (4) given below.

[Equation 4]

$$\left.\begin{array}{l} y_0 = h_0 x_0 \\ y_1 = h_0 x_1 + h_1 x_0 \\ y_2 = h_0 x_2 + h_1 x_1 + h_2 x_0 \end{array}\right\} \quad (4)$$

According to the equation (4), each component $h_{i-j}$ of the transfer function may be calculated by using the least squares method or the like with the equation (4) as a set of simultaneous equations for $h_j$.

Figure 9:
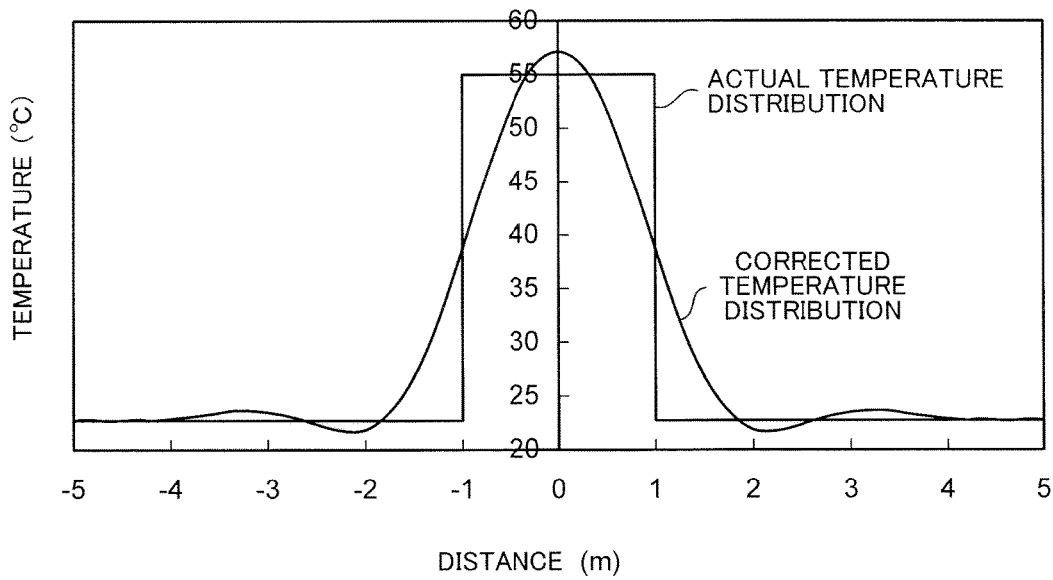
FIG. 9 is a graph illustrating a stepped actual temperature distribution and a measured temperature distribution corresponding thereto which are used for finding each component of a transfer function.

A stepped actual temperature distribution and a measured temperature distribution corresponding thereto as illustrated in FIG. 9, for example, may be used as the actual temperature distribution x and the measured temperature distribution y for finding each component $h_{i-j}$ of the transfer function.

Note that the transfer function h not only varies with the distance from the light source but also differs with the material of the optical fiber 24, the pulse response characteristics of the temperature distribution measurement apparatus 20, and the like. For this reason, it is preferable to acquire the measured temperature distribution under the same condition as the actual temperature measurement when finding each component $h_{i-j}$ of the transfer function.

Meanwhile, focusing on the equation (3) in a region where the temperature changes, the regions before and after this region are regions where the temperature does not change. Then, the components $x_i$ and $y_k$ in these regions are 0 and are therefore meaningless components which are not important in the equation (3) for calculation. For this reason, a column vector with the components of the equation (2) excluding all the components with a value of 0 before and after the region of interest where the temperature changes, is expressed as the equation (5) given below. Note that t represents a transposed matrix.

[Equation 5]

$$x = (x_0, x_1, x_2, \ldots, x_n)^t \quad (5)$$

Moreover, similarly for the measured temperature distribution, the components with a value of 0 in each region where the temperature does not change are meaningless components which are not important for calculation. Thus, a column vector with the components of the equation (1) excluding all the components with a value of 0 before and after the region of interest where the temperature changes, is expressed as the equation (6) given below.

[Equation 6]

$$y = (y_0, y_1, y_2, \ldots, y_m)^t \quad (6)$$

The numbers of components in the column vectors of the equations (5) and (6) are n+1 and m+1, respectively, but m is greater than n (m>n). This is because, as illustrated in FIG. 9, the measured temperature distribution spreads horizontally wider than the actual temperature distribution, and the measured temperature distribution therefore has a larger number of components which are not 0.

In the case where the equation (4) is expressed in the form of the equation (7) given below with the actual temperature distribution x and the measured temperature distribution y as finite-dimensional column vectors like the equations (5) and (6), a matrix [H] is created based on the transfer function h and has a finite number of components which is (m+1)×(n+1). The matrix [H] thus created will be referred to as a matrix representation of the transfer function.

[Equation 7]

$$y = [H]x \quad (7)$$

Note that the dimension of each of the column vectors x and y in the equation (7) is a finite dimension like the equations (5) and (6).

In the equation (7), the components $y_i$ of y are m+1 values obtained by the temperature measurement, and [H] may be regarded as a (m+1)×(n+1) coefficient matrix of the set of simultaneous equations. Since there is the relationship m>n as mentioned above, this set of simultaneous equations is not uniquely solved for x.

Then, a squared error e as described in the equation (8) given below is considered.

[Equation 8]

$$e = \|y - [H]X\|^2 = (y - [H]X)^t (y - [H]X) \quad (8)$$

Note that like the actual temperature distribution, the column vector X in the equation (8) is an n-dimensional vector having components as described in the equation (9) given below.

[Equation 9]

$$X = (X_0, X_1, X_2, \ldots, X_n)^t \quad (9)$$

A distribution X which reduces the squared error e in the equation (8) approximately satisfies the equation (9) as well. As the squared error e in the equation (8) decreases, the accuracy of the approximation increases accordingly and the distribution X becomes accordingly closer to the actual temperature distribution x. Hereinafter, the distribution X will be referred as the corrected temperature distribution of the measured temperature distribution y. According to this, the equation (8) may be said to be an equation for calculating the squared error e between convolution of the transfer function h and the corrected temperature distribution of the optical fiber 24 along the path along which it is laid, and the measured temperature distribution y.

To find a corrected temperature distribution X which reduces the squared error e as much as possible, a gradient vector $\partial e/\partial X$ of the squared error e is calculated from the equation (10) given below based on the equation (8).

[Equation 10]

$$\frac{\partial e}{\partial X} = \begin{bmatrix} \frac{\partial e}{\partial X_1} \\ \frac{\partial e}{\partial X_2} \\ \vdots \\ \frac{\partial e}{\partial X_n} \end{bmatrix} = \frac{\partial}{\partial X} \|y - [H]X\|^2 \quad (10)$$

$$= -2[H]^t (y - [H]X)$$

$$= -2([H]^t y - [H]^t [H]X)$$

Determining each component Xi of X such that the gradient vector $\partial e/\partial X$ may be 0 corresponds to the least squares method.

Note that the diagonal components of $[H]^t[H]$ in the equation (10) may be subtly increased in consideration of noise during the measurement. In this way, it is possible to suppress increase in the high-frequency component of the noise and enhance the margin resistance. The correction by the inverse filter mentioned above (see FIG. 6) is equivalent to this correction achieved through the calculation by the least squares method.

Here, the gradient vector ∂e/∂X indicates a direction in which the squared error e increases. Then, the squared error e decreases by shifting in the opposite sign direction −∂e/∂X.

For this reason, X is sequentially corrected as described in the equation (11) given below.

[Equation 11]

$$X^{(k+1)} = X^{(k)} - \alpha \frac{\partial e}{\partial X}\bigg|_{X=X^{(k)}} \quad (11)$$

Here, k denotes the number of iterations of the correction, and $X^{(k)}$ denotes the corrected temperature distribution after the correction is performed k times. The components of this $X^{(k)}$ may be expressed as the equation (12) given below.

[Equation 12]

$$X^{(k)} = (X_0^{(k)}, X_1^{(k)}, \ldots, X_n^{(k)})^t \quad (12)$$

Moreover, α is a positive correction coefficient which makes the equation (11) convergent, and may be empirically selected from a range of 0.5 to 1. The following calculation will be done with a set at 0.5.

Moreover, $X^{(0)}$, which is the initial value, is a null vector, and the equation (10) with the diagonal components of $[H]^t[H]$ subtly increased is used for the calculation of ∂e/∂X in the equation (11).

Through iterative calculations using the equation (11), a corrected temperature distribution $X^{(k+1)}$ which reduces the squared error e to a greater extent than $X^{(k)}$ does is calculated sequentially a plurality of times.

Meanwhile, as described with reference to FIG. 2, the temperature at each of the plurality of measurement points i present within each section G on the path along which the optical fiber 24 is laid is the same as the temperature at the middle point P. Thus, each time the correction calculation by the equation (11) is performed, the components $X_i^{(k)}$ corresponding to the plurality of measurement points i at the winding parts 24x or 24y in the section G are replaced with the measured temperature at the middle point P.

As described when the equations (5) and (6) are defined, each component of the column vectors x, y and X is found by subtracting the measured temperature $T_{AB}$ at the middle point P from the actual value. Thus, the value of each replaced component $X_i^{(k)}$ is 0 (=$T_{AB}-T_{AB}$).

This 0 (=$T_{AB}-T_{AB}$) found based on the measured temperature $T_{AB}$ is the value of the component at a measurement point equivalent to the middle point P among the plurality of components $y_i$ of the measured temperature distribution y, and means a common estimated temperature within the section G.

Note that the common estimated temperature within the section G is not limited to the temperature of 0 (=$T_{AB}-T_{AB}$) mentioned above. For example, the average of a plurality of components $y_i$ of the measured temperature distribution y corresponding to a plurality of measurement points i in a region on the winding part 24x or 24y where the actual temperature is measured, may be used as an estimated temperature common to these measurement points. In this case, the length $D_3$ of the portion of the optical fiber 24 wound around the winding part 24x or 24y may be made longer than 2.3 m mentioned above. This increases the number of measurement points i in the region on the winding part 24x or 24y where the actual temperature is measured, and thereby improves the accuracy of the temperature estimation. Further, making the length $D_3$ longer as described above may also provide even lesser susceptibility to the influence of the temperature of the adjacent rack 11.

Moreover, as described with reference to FIG. 2, the overlapping points $H_1$ and $H_2$ at which the temperature may be assumed to be the same are present on the portions of the optical fiber 24 extending between the winding parts 24x and 24y and the winding part 24z. Thus, for these overlapping points, too, each time the correction calculation by the equation (11) is performed, components $X_{i1}^{(k)}$ and $X_{i2}^{(k)}$ of the corrected temperature distribution at the overlapping points $H_1$ and $H_2$ are replaced with an average $X_{avg1}$ (=$(X_{i1}^{(k)}+X_{i2}^{(k)})/2$) of the corrected temperatures at the overlapping points $H_1$ and $H_2$. These corrected temperatures $X_{i1}^{(k)}$ and $X_{i2}^{(k)}$ are the values of the components at measurement points $i_1$ and $i_2$ equivalent to the overlapping points $H_1$ and $H_2$ among the plurality of components $X_i^{(k)}$ of the corrected temperature distribution $X^{(k)}$, and their average $X_{avg1}$ means an estimated temperature common to the overlapping points $H_1$ and $H_2$.

Further, similarly to the above, for the plurality of overlapping points $K_i$ on the winding part 24z, too, each time the correction calculation by the equation (11) is performed, the components $X_i^{(k)}$ of the measured temperature distribution at the overlapping points $K_i$ are replaced with an average $X_{avg2}$ of the corrected temperatures $X_i^{(k)}$ at the overlapping points $K_i$. Similarly to the above, these corrected temperatures $X_i^{(k)}$ are the values of the components at the measurement points i equivalent to the overlapping points $K_i$ among the plurality of components $X_i^{(k)}$ of the corrected temperature distribution $X^{(k)}$. Their average $X_{avg2}$ then means an estimated temperature common to the overlapping points $K_i$.

Assume, for example, that the intervals of the measurement points set in the length direction of the optical fiber 24 are 0.1 m. In this case, if the length of the portion of the optical fiber 24 wound around the winding part 24z is 0.5 m, the number of overlapping points $K_i$ is five (=0.5 m/0.1 m).

Then, components $X_{i-2}^{(k)}$, $X_{i-1}^{(k)}$, $X_i^{(k)}$, $X_{i+1}^{(k)}$, and $X_{i+2}^{(k)}$ of the corrected temperature distribution at these overlapping points $K_{i-2}$, $K_{i-1}$, $K_i$, $K_{i+1}$, and $K_{i+2}$ are replaced with the average $X_{avg2}$ of the corrected temperatures $X_{i-2}^{(k)}$, $X_{i-1}^{(k)}$, $X_i^{(k)}$, $X_{i+1}^{(k)}$, and $X_{i+2}^{(k)}$ at these points (=$(X_{i-2}^{(k)}+X_{i-1}^{(k)}+X_i^{(k)}+X_{i+1}^{(k)}+X_{i+2}^{(k)})/5$) each time the correction calculation is performed.

Meanwhile, the temperature at each of the plurality of measurement points i on the winding parts 24x and 24y is $T_{AB}$. As mentioned when the equations (5) and (6) are defined, the value of each component of the column vectors x, y, and X is obtained by subtracting this $T_{AB}$ from the actual temperature value. Then, a final corrected temperature distribution $T_{iomp-i}$ is found by adding the temperature $T_{AB}$ as described in the equation (13) given below after the calculation is iterated as needed (n times) for the equation (12).

[Equation 13]

$$T_{iomp\_i} = X_i^{(n)} + T_{AB} \quad (13)$$

Moreover, the temperature of the portions of the optical fiber 24 around the winding parts 24x and 24y is prevented from rising by the cool air. On the other hand, the temperature of the other portion of the optical fiber 24 does not fall below the temperature of the portions around the winding parts 24x and 24y since the other portion is situated above the floor 12 where the temperature is higher than the free access floor 15.

This condition is expressed as the equation (14) given below.

[Equation 14]

$$X_i^{(k)} \geq 0 \quad (14)$$

If there is any component less than 0 ($X_i^{(k)} < 0$) at the k-th calculation by the equation (11), that component $X_i^{(k)}$ is set to 0 and the k+1-th calculation is then performed.

As described above, in the case where the temperature measurement area includes a portion where the temperature is known to be equal to or higher than a predetermined temperature, the temperature at this portion after the correction by the equation (11) may be replaced with the predetermined temperature when the corrected temperature at the portion falls below the predetermined temperature.

On the other hand, in the case where the temperature measurement area includes a portion where the temperature is known to be equal to or lower than a predetermined temperature, the temperature at this portion after the correction by the equation (11) may be replaced with the predetermined temperature when the corrected temperature at the portion exceeds the predetermined temperature.

In step S2, the correction calculation is iteratively performed by using the equation (11) as described above, and the final corrected temperature distribution $T_{iomp-i}$ is found from $X_i^{(n)}$ at the point where an index indicative of the amount of decrease in squared error e, e.g., $e^{(n)} - e^{(n-1)}$, reaches or falls below a predetermined value. Note that $e^{(n)}$ is a squared error found from the equation (8) by using $X^{(n)}$ obtained by performing the correction by the equation (11) n times.

Next, the advantage achieved by the above replacement will be described.

Figure 10:
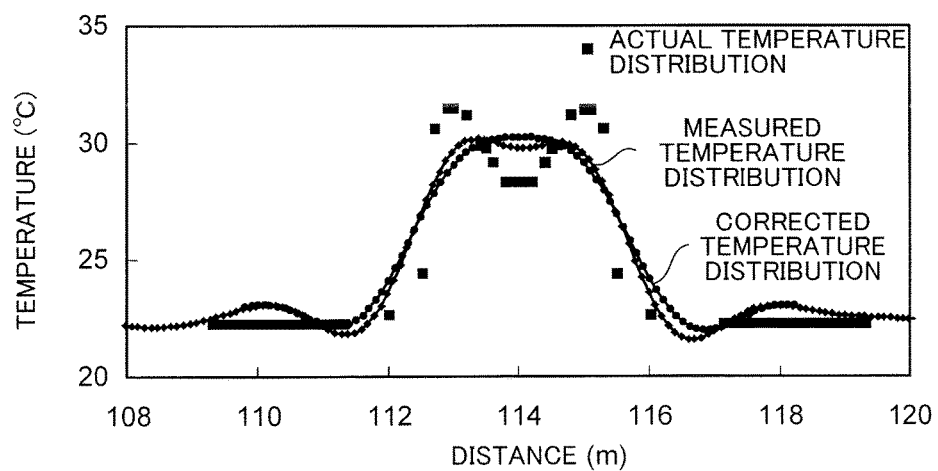
FIG. 10 is a graph illustrating the effect of super-resolution signal processing (part 1)
Figure 11:
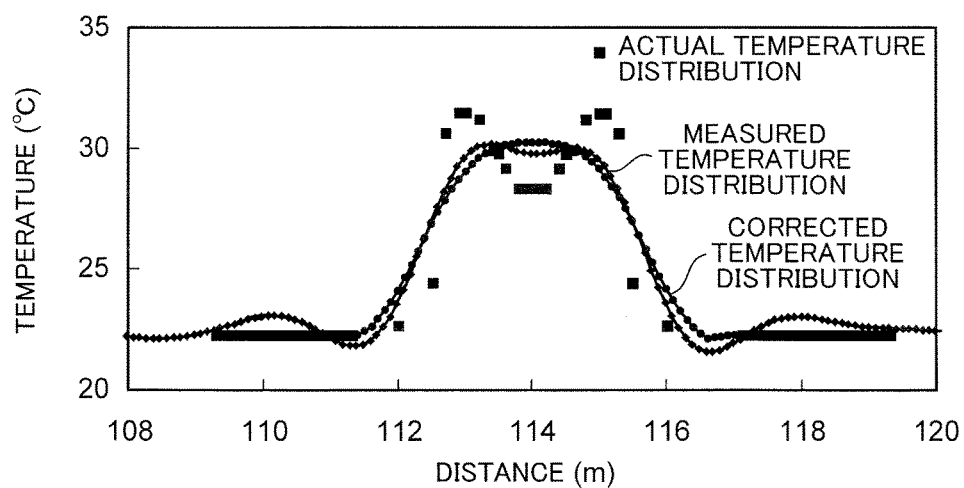
FIG. 11 is a graph illustrating the effect of the super-resolution signal processing (part 2)
Figure 12:
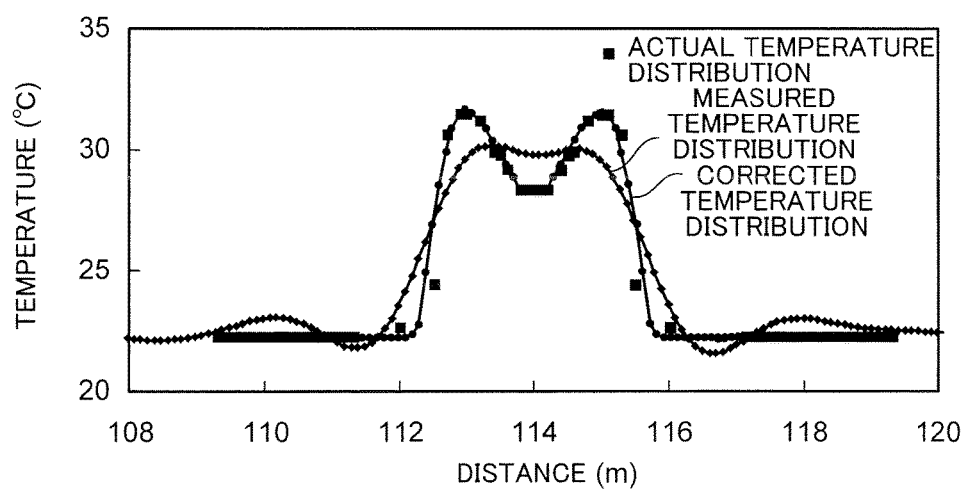
FIG. 12 is a graph illustrating the effect of the super-resolution signal processing (part 3)

FIGS. 10 to 12 are graphs illustrating the effect of the super-resolution signal processing described above. In FIGS. 10 to 12, the horizontal axis represents the distance from the end of the optical fiber 24 while the vertical axis represents temperature.

FIG. 10 is a graph after performing the correction by the equation (11) once. As illustrated in this FIG. 10, one correction does not solve the departure of the corrected temperature distribution from the actual temperature distribution.

FIG. 11 is a graph after performing the replacement described above for each region and each section G and the points $H_1$, $H_2$, and $K_i$ after performing the correction once. As illustrated in this FIG. 11, the temperature value of the corrected temperature distribution is substantially the same as the actual temperature distribution at the portions where the replacement is performed.

FIG. 12 is a graph after such correction calculation is iterated 100 times. As illustrated in this FIG. 12, the corrected temperature distribution substantially coincides with the actual temperature distribution by performing the correction calculation 100 times.

Embodiment

Figure 13:
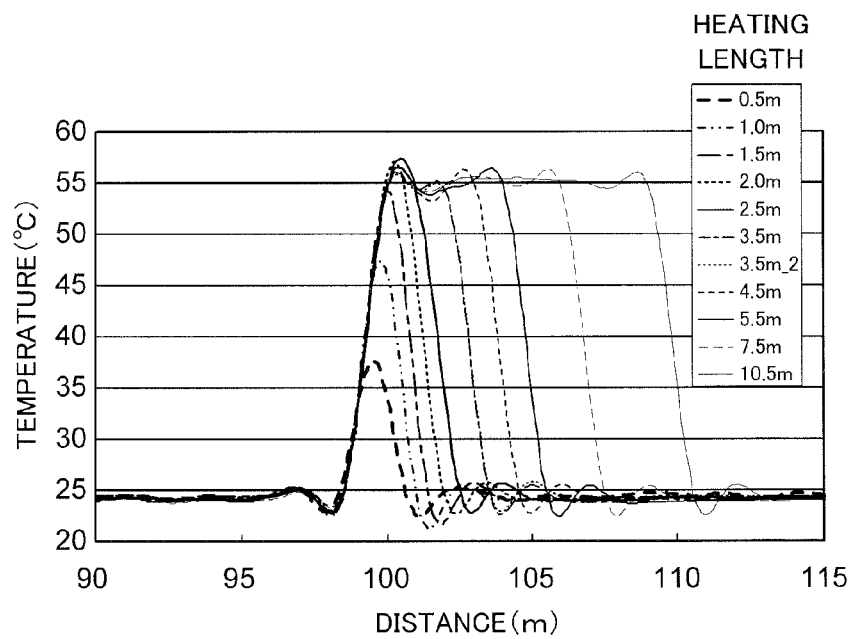
FIG. 13 is a graph illustrating a temperature distribution acquired by a temperature distribution measurement apparatus in a situation where a given section of an optical fiber is heated to 55° C. under a 25° C. environment.

FIG. 13 is a graph illustrating a temperature distribution acquired by a temperature distribution measurement apparatus in a situation where a given section of an optical fiber is heated to 55° C. under a 25° C. environment. FIG. 13 indicates that the temperature detected by the temperature distribution measurement apparatus is about 37° C. in the case where the heating length is 50 cm, for example.

The temperature measurement system exemplarily illustrated in FIG. 2 is capable of acquiring the temperature distribution inside a datacenter with high accuracy as mentioned above. Doing so, however, uses a condition that an optical fiber of the minimum heating length or longer is disposed in a location where the temperature is constant, and a condition that an upper limit or lower limit value of temperature at measurement points in a range of interest is determined.

As is clear from FIG. 13, in the case of a temperature distribution measurement apparatus using an optical fiber as a sensor, the sensitivity deteriorates if the heating length is shorter than the minimum heating length. For this reason, even when one uses a temperature distribution measurement apparatus in an attempt to detect temperature change originating from abnormality in a facility such as a chemical plant, it is difficult to detect the abnormality at an early stage where the temperature change occurs to a small extent, if it is difficult to dispose an optical fiber of the minimum heating length or longer at the measurement spot.

Moreover, it is also difficult to determine an upper limit or lower limit value of temperature for a facility such as a chemical plant.

Further, the following problem also arises in the case of applying an optical fiber-type temperature distribution measurement apparatus to the detection of abnormality which occurs in a facility such as a chemical plant.

Figure 14:
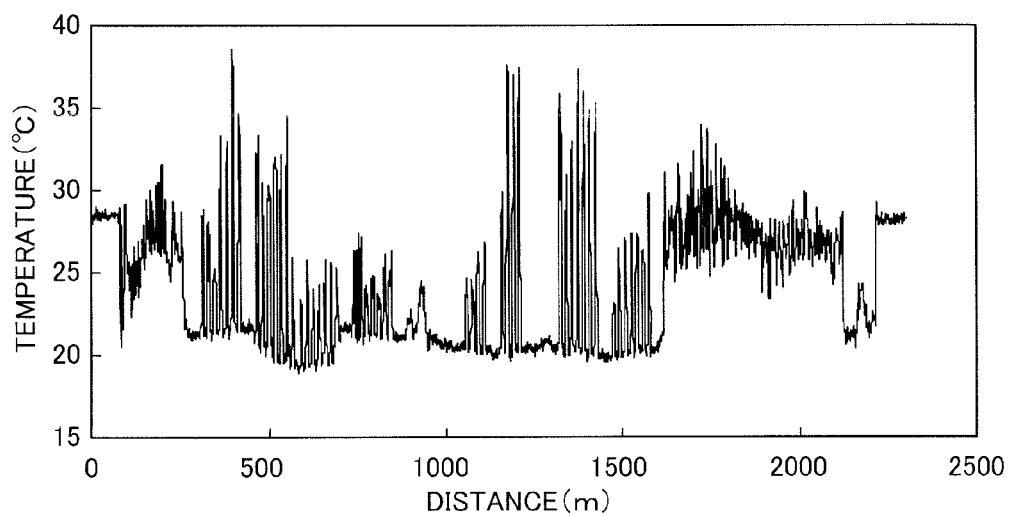
FIG. 14 is a graph illustrating the result of measuring the temperature distribution inside a room.

FIG. 14 is a graph with the horizontal axis representing the distance from an end of an optical fiber versus the vertical axis representing temperature, illustrating the result of measuring the temperature distribution inside a room. As illustrated in this FIG. 14, the length of the optical fiber used for the temperature distribution measurement is several km, and the temperature distribution is complicated as well.

In the case of the data center illustrated in FIG. 2, the winding parts 24x and 24y are provided between the racks 11, thereby preventing interference between the adjacent racks 11. For this reason, it is possible to acquire an accurate temperature distribution by performing a correction process for each rack 11, and automate the correction process with a data processing unit. Without any winding parts, however, it is difficult to automate the correction process since it is impossible to determine the unit length by which the correction process may be performed.

Hereinbelow, a temperature measurement system usable for abnormality detection in a facility such as a chemical plant will be described.

Figure 15:
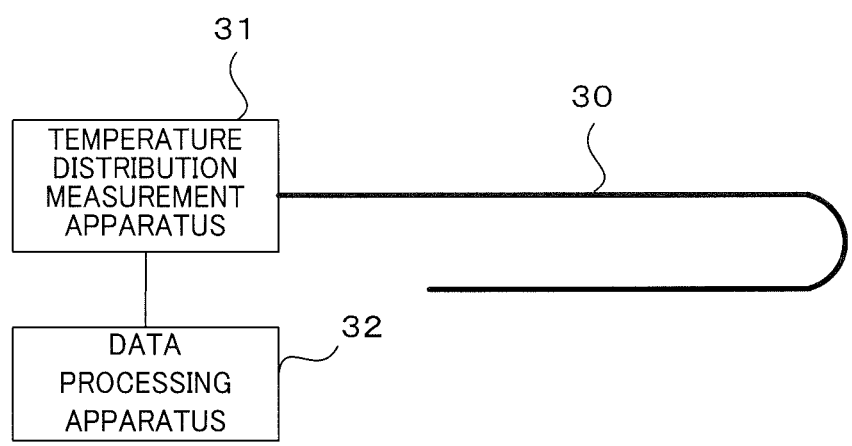
FIG. 15 is a block diagram illustrating the configuration of a temperature measurement system according to an embodiment.

FIG. 15 is a block diagram illustrating the configuration of a temperature measurement system according to an embodiment. As illustrated in this FIG. 15, the temperature measurement system according to the embodiment includes an optical fiber 30, a temperature distribution measurement apparatus (DTS) 31, and a data processing apparatus 32.

The temperature distribution measurement apparatus 31 is configured to output laser of a predetermined pulse width at regular intervals to the optical fiber 30. The temperature distribution measurement apparatus 31 is configured to then detect Raman scattered light (Stokes light and anti-Stokes light) generated in the optical fiber 30 and acquire the temperature distribution of the optical fiber 30 in the length direction based on the result of the detection. The temperature distribution measurement apparatus 31 may be a single end type to which one end of the optical fiber 30 is connected or a loop type to which both ends of the optical fiber 30 are connected.

The data processing apparatus 32 includes a computer as its constituent component. The data processing apparatus 32 is configured to determine the presence of abnormality by performing signal processing in a manner described below on data on the temperature distribution acquired by the temperature distribution measurement apparatus 31, and perform a preset process such as putting out an alert if determining that abnormality is present.

The temperature measurement system according to this embodiment determines the presence of abnormality based not on temperature but on change in temperature. Moreover, the temperature measurement system according to this embodiment determines the range within which to perform the signal processing, based on the time-series change in the temperature distribution acquired by the temperature distribution measurement apparatus 31.

Figure 16:
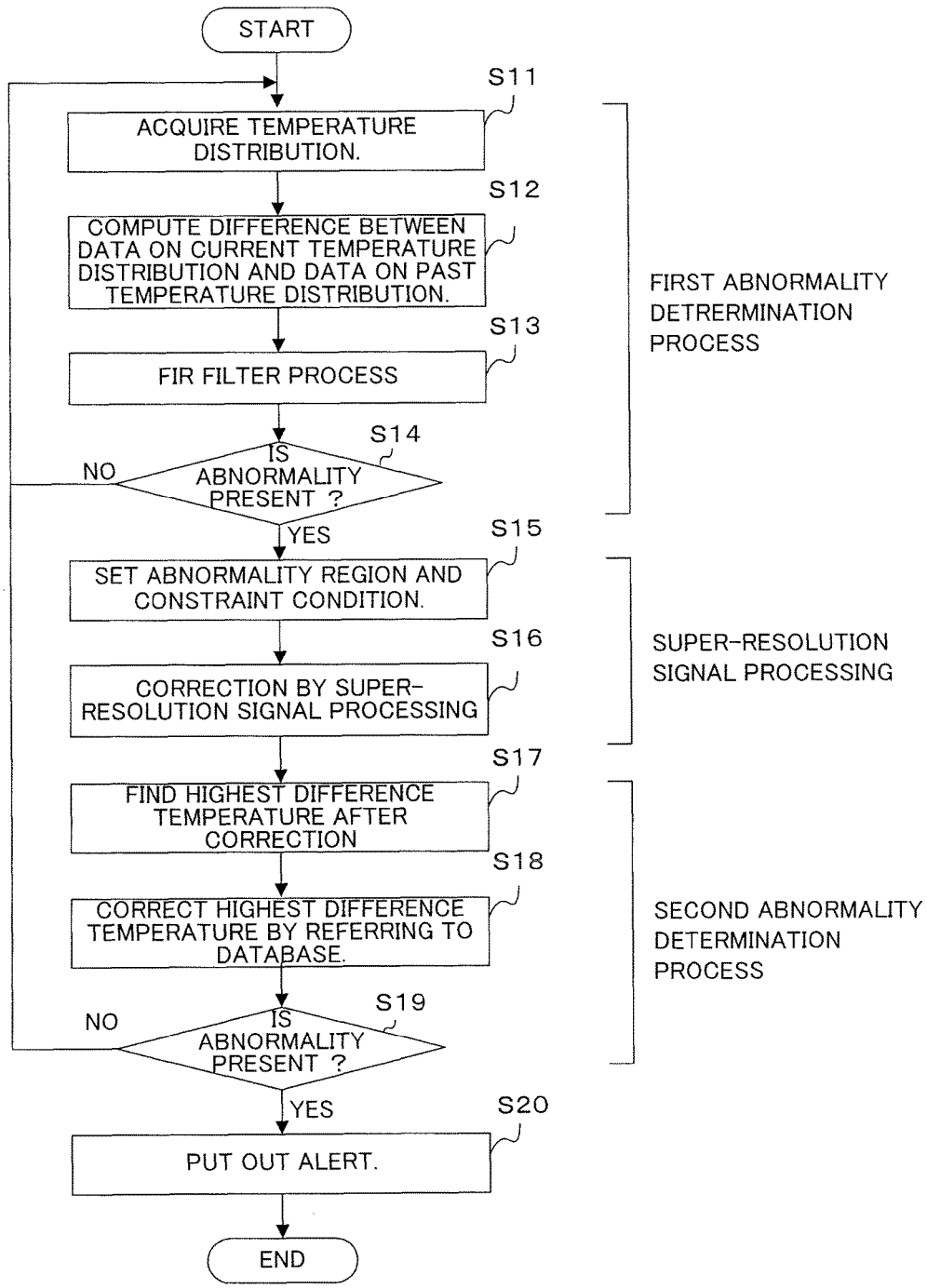
FIG. 16 is a flowchart describing an abnormality detection method using the temperature measurement system according to the embodiment.

FIG. 16 is a flowchart describing an abnormality detection method using the temperature measurement system according to this embodiment.

In this embodiment, a first abnormality determination process (steps S11 to S14) is performed to determine the presence of a spot where abnormality may possibly have occurred, and super-resolution signal processing (steps S15 and S16) is performed if there is a spot where abnormality may possibly have occurred. After the super-resolution signal processing, a second abnormality determination process (steps S17 to S19) is performed to determine the presence of abnormality, and a process such as putting out an alert or the like is performed if abnormality is determined to be present. A more detailed description will be given below.

First, in step S11, the data processing apparatus 32 acquires data on the temperature distribution at the current point from the temperature distribution measurement apparatus 31 (hereinafter, referred to as the current temperature distribution). The data on the current temperature distribution thus acquired is stored in the data processing apparatus 32.

Then, in step S12, the data processing apparatus 32 obtains the difference between the data on the current temperature distribution acquired in step S11 and data on a past temperature distribution stored in the data processing apparatus 32 (hereinafter, referred to as the past temperature distribution) (hereinafter, the difference will be referred to as the difference temperature distribution).

In this case, the data on the past temperature distribution is calculated preferably by weighting pieces of data on temperature distributions at a plurality of past times, for example. Specifically, the temperature at a position Y is calculated from the equation (15) given below, where T is the current time and $\Delta T$ is the measurement interval.

$$a \times ((1/2)Y(T-\Delta T)+(1/4)Y(T-2\Delta T)+(1/8)Y(T-3\Delta T)+(1/16)Y(T-4\Delta T)+(1/32)Y(T-5\Delta T)+ \ldots ) \quad (15)$$

Note that the value of a is 1 in the case of using data on a single past temperature distribution. The value of a is adjusted such that the sum of the coefficients may be 1 in the case of using data on a plurality of past temperature distributions.

Figure 17:
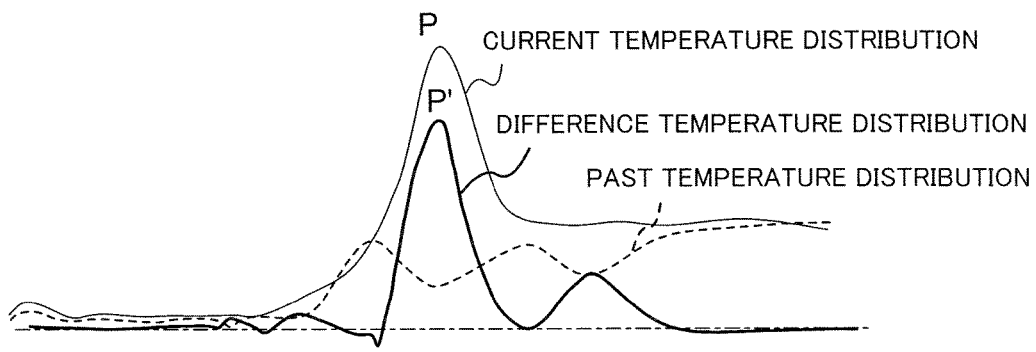
FIG. 17 is a graph illustrating a current temperature distribution, a past temperature distribution, and a difference temperature distribution.

FIG. 17 is a graph illustrating a current temperature distribution, a past temperature distribution, and a difference temperature distribution. Here, it is assumed that some abnormality has occurred, and a large peak P, which is not on the past temperature distribution, appears on the current temperature distribution.

Then, a peak P' originating from the abnormality appears on the difference temperature distribution which is the difference between the current temperature distribution and the past temperature distribution. However, the difference temperatures at locations away from the peak P' by a certain distance are substantially 0.

As mentioned above, the temperature distribution acquired by the temperature distribution measurement apparatus may be said to be the result of applying a transfer function to the actual temperature distribution. The transfer function varies as the optical fiber, the laser light source, and the like vary with time. However, the transfer function may be considered to be constant over a sufficiently longer time than the time for which temperature change occurs due to abnormality. Moreover, the transfer function varies depending on the location in the length direction of the optical fiber. However, the transfer function may be considered to be constant within a range of several tens of cm to several tens of m which is used for abnormality detection.

For this reason, the value of the difference temperature may be assumed to be 0 at locations away from an abnormality spot (heat source), which causes a peak, by the distance to the zero point $X_3$ on the transfer function (see FIG. 4) or longer.

Then, in step S13, the data processing apparatus 32 acquires a standard deviation by applying (convoluting) an FIR (Finite Impulse Response) filter, which is a type of a window function, to the difference temperature distribution. Specifically, the difference temperature distribution is differentiated in the length direction of the optical fiber, and the FIR filter is then applied. The range of the difference temperature distribution within which it is differentiated is, for example, a range being centered at the peak and equal to the heating length plus ±4 m, in consideration of the zero point $X_3$ on the transfer function.

Figure 18:
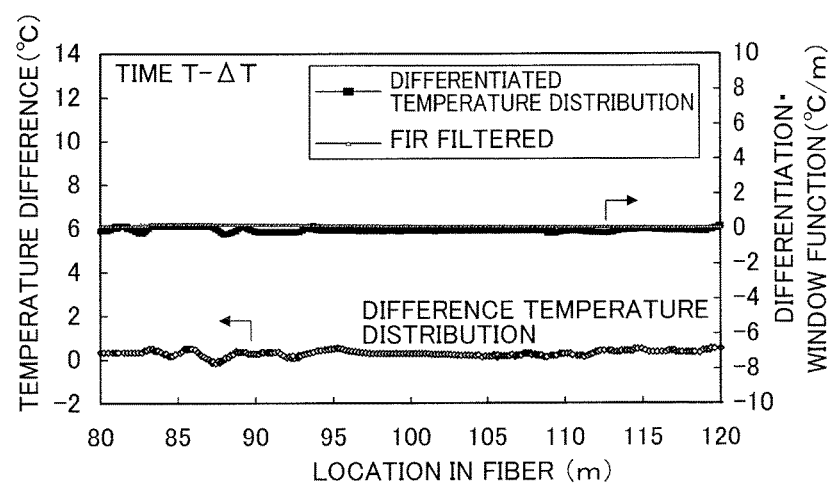
FIG. 18 is a graph illustrating a difference temperature distribution before abnormality occurs, a differentiated temperature distribution obtained by differentiating the difference temperature distribution, and a temperature distribution obtained by applying an FIR filter.

FIG. 18 illustrates a difference temperature distribution before abnormality occurs, i.e. at a time T−ΔT, a differentiated temperature distribution obtained by differentiating the difference temperature distribution, and a temperature distribution obtained by applying an FIR filter (FIR filtered).

Figure 19:
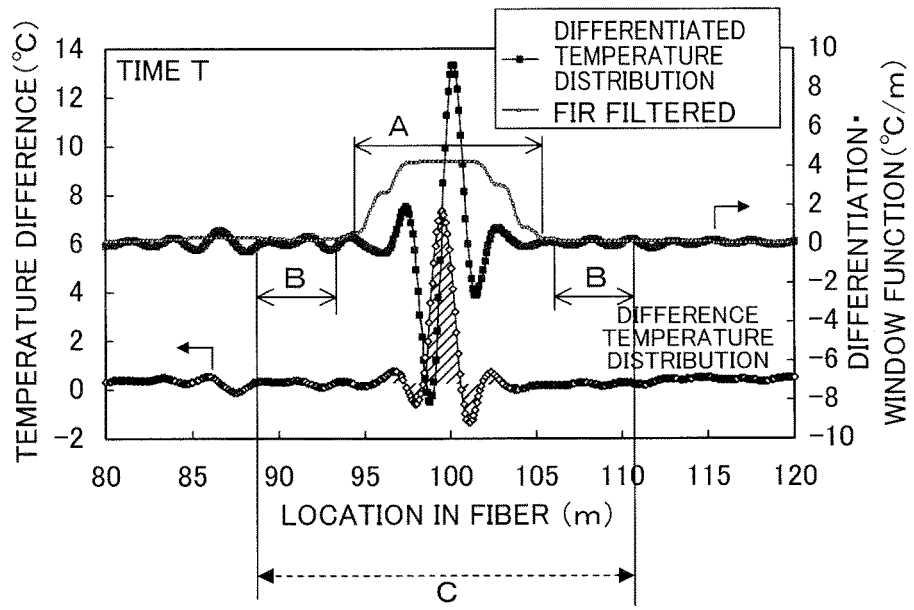
FIG. 19 is a graph illustrating a difference temperature distribution at the occurrence of abnormality, a differentiated temperature difference distribution obtained by differentiating the difference temperature distribution, and a temperature difference distribution obtained by applying the FIR filter.

Moreover, FIG. 19 illustrates a difference temperature distribution at the occurrence of abnormality, i.e. at a time T, a differentiated temperature difference distribution obtained by differentiating the difference temperature distribution, and a temperature difference distribution obtained by applying the FIR filter (FIR filtered).

As is clear from FIGS. 18 and 19, the difference temperature is substantially 0 over the entire range in the length direction of the optical fiber when there is no abnormality, and a peak appears on the difference temperature distribution when abnormality occurs. When the difference temperature distribution on which this peak has appeared is differentiated in the length direction of the optical fiber, a graph (differentiated temperature distribution) is obtained which oscillates in the negative and positive directions in accordance with the gradient of the peak. A substantially trapezoidal peak appears when the FIR filter is convoluted with this graph in the length direction of the optical fiber.

Proceeding then to step S14, the data processing apparatus 32 determines the presence of abnormality. The presence of abnormality may be determined based on whether or not a peak above a threshold is present on the difference temperature distribution or based on whether or not a value above a threshold is present on the graph obtained by applying the FIR filter.

If determining in step S14 that no abnormality is present, the data processing apparatus 32 returns to step S11 and continues the process. On the other hand, if determining in step S14 that abnormality is present, the data processing apparatus 32 proceeds to step S15.

As will be described later, in this embodiment, the second abnormality determination process is performed in consideration of the normal, long-term temperature change, and a process such as putting out an alert or the like is performed when it is determined by the second abnormality determination process that abnormality is present. However, the process such as putting out an alert or the like may be performed when it is determined in step S14 that abnormality is present.

In step S15, an abnormality region is set and a constraint condition is set as well. As illustrated in FIG. 19, in the case where abnormality has occurred, a trapezoidal peak appears on the graph obtained by applying the FIR filter. The region of this trapezoidal peak will be referred to as an abnormality region A, and certain ranges outside the abnormality region A will be referred to as reference temperature regions B. In addition, a region covering both the abnormality region A and the reference temperature regions B will be referred to as a signal processing region C. Setting the signal processing region C in this manner determines the number of elements (the number of rows and the number of columns in terms of matrix) to which to apply the transfer function.

On the other hand, the constraint condition is set as follows. Specifically, in the case where abnormality occurs in a chemical plant or the like, the abnormality is either one that causes temperature increase with time or one that causes temperature decrease with time. Based on whether the integrated value of the difference temperature within the abnormality region is positive or negative, it is possible to determine whether the abnormality is one that causes temperature increase with time or one that causes temperature decrease with time. Hereinafter, the case where the integrated value of the difference temperature distribution is positive will be referred to as the non-negative constraint, and the case where the integrated value of the difference temperature distribution is negative will be referred to as the non-positive constraint.

Proceeding then to step S16, the data processing apparatus 32 corrects the difference temperature distribution by using the super-resolution signal processing described above. Specifically, assuming that the reference temperature regions B are equivalent to the winding parts, the data processing apparatus 32 applies the equation (6) previously described in the prelude to the abnormality region A and iteratively performs the correction by the equation (11).

Figure 20:
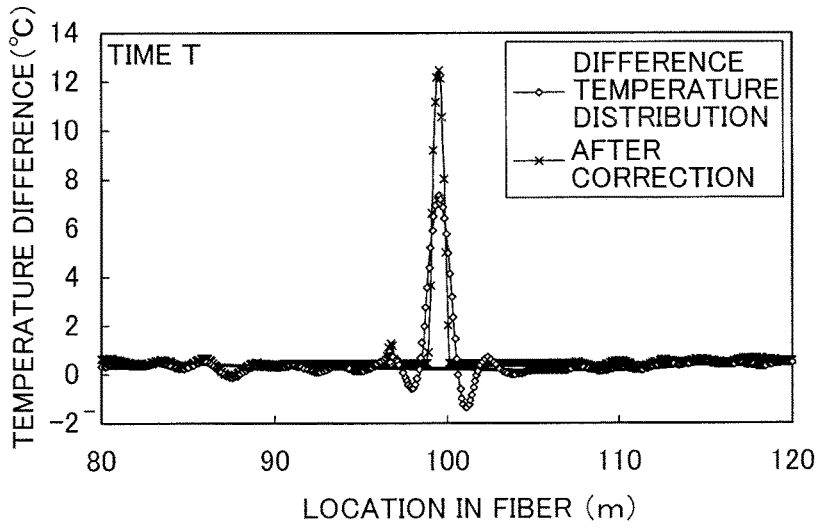
FIG. 20 is a graph illustrating the result of performing the super-resolution signal processing while assuming an abnormality region A as a finite measured temperature distribution region under a non-negative constraint.

FIG. 20 is the result of performing the super-resolution signal processing while assuming the abnormality region A as a finite measured temperature distribution region under the non-negative constraint. In the example illustrated in this FIG. 20, a peak approximately 1.8 times higher than the difference temperature peak is obtained. In other words, the sensitivity to temperature difference may be said to be increased by 1.8 times.

For example, in the case where the heating length of the optical fiber is 50 cm and the temperature difference between the heating section and other sections is 50° C., the temperature distribution measurement apparatus may detect a temperature difference of about 22° C., but may detect a temperature difference of approximately 41° C. with the super-resolution signal processing.

The width of the trapezoidal peak (trapezoidal function) illustrated in FIG. 19 limits the sizes of m and n given in the equations (5) and (6). For example, appropriate m and n are set each time the abnormality range is set in the iterative correction during the super-resolution signal processing.

Note that the targets here are not the temperature distributions y and x but temperature difference distributions $\Delta y$ and $\Delta x$. Thus, y and x in the previous explanation of the prelude need to be replaced with $\Delta y$ and $\Delta x$, respectively.

Then, in steps S17 to S19, the second abnormality determination process is performed.

The temperatures at the measurement spots may change with season or hour, for example. For this reason, in this embodiment, the presence of abnormality is determined by taking into consideration the temperature change with season, hour, or the like. Specifically, the data processing apparatus 32 acquires the average temperature of a region twice wider than the signal processing region C from the data on the temperature distribution outputted from the temperature distribution measurement apparatus 31, regularly at a predetermined time, for example. The data processing apparatus 32 then creates a database by accumulating one year's data, for example.

In step S17, the data processing apparatus 32 finds the highest difference temperature after the correction within the abnormality region A. Then, proceeding to step S18, the data processing apparatus 32 reads out the average temperature of the reference temperature regions B obtained a year, month, or day ago at the same time (or the closest time), for example, from the database, and corrects (offsets) the highest difference temperature.

In step S19, the data processing apparatus 32 compares the highest difference temperature after the correction with a preset value (threshold) to determine the presence of abnormality. If determining that no abnormality is present, the data processing apparatus 32 returns to step S11 and continues the process. On the other hand, if determining in step S19 that abnormality is present, the data processing apparatus 32 proceeds to step S20 and performs a preset process such as putting out an alert.

In this way, it is possible to detect abnormality at an early stage, the abnormality occurring in a facility such as a chemical plant, an oil refinery plant, or a thermal power plant.

Figure 21:
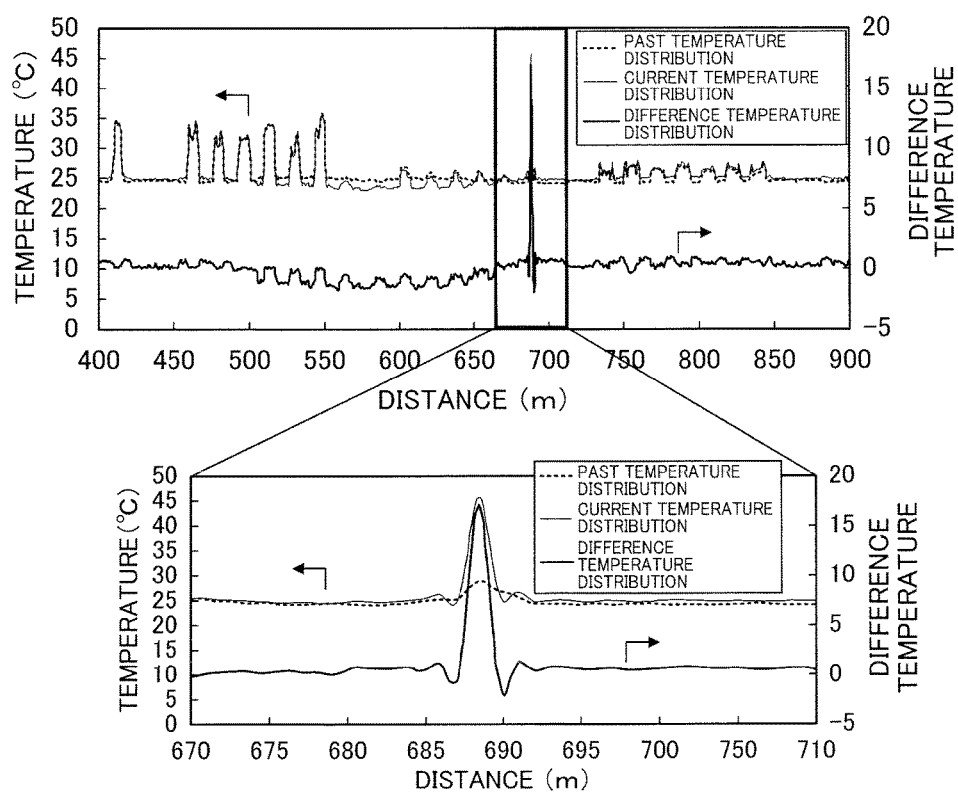
FIG. 21 is a set of graphs illustrating a current temperature distribution, a past temperature distribution, and a difference temperature distribution.

(Discussion) FIG. 21 is a set of graphs each with the horizontal axis representing the distance from an end of an optical fiber versus the vertical axis representing measured temperature and difference temperature, illustrating a current temperature distribution, a past temperature distribution, and a difference temperature distribution. In this example, the past temperature distribution is acquired and a portion of the optical fiber is then heated by a length of 80 cm.

Figure 22:
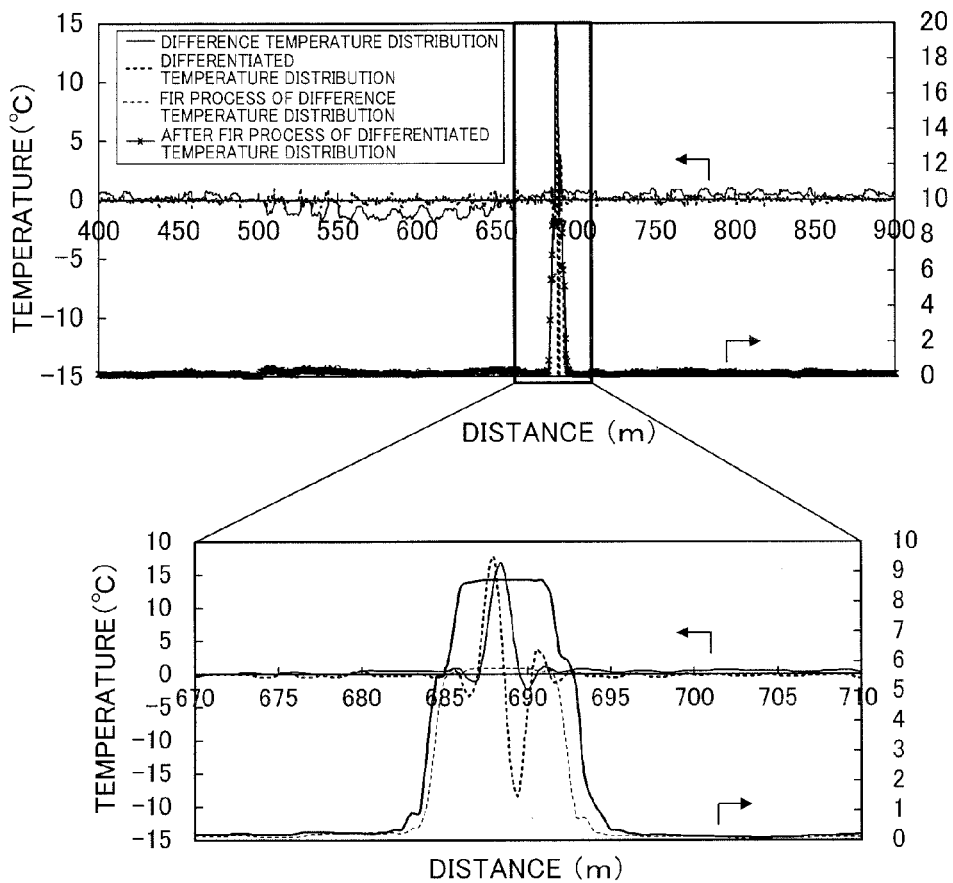
FIG. 22 is a set of graphs illustrating the difference temperature distribution, together with a differentiated temperature distribution obtained by differentiating the difference temperature distribution, the result of applying an FIR filter to the difference temperature distribution, and the result of applying the FIR filter to the differentiated temperature distribution.

FIG. 22 is a set of graphs illustrating the difference temperature distribution in FIG. 21, together with a differentiated temperature distribution obtained by differentiating the difference temperature distribution, the result of applying an FIR filter to the difference temperature distribution, and the result of applying the FIR filter to the differentiated temperature distribution. In FIG. 22, the abnormality range is found by applying an FIR filter which finds a standard deviation in a range of ±3.5 m from the peak center.

Here, the range to which to apply the FIR filter is set to a range of ±3.5 m from the peak center because a range within which the transfer function in FIG. 4 may be assumed to reach substantially zero is ±4 m, and a range narrower than that is therefore set as an effective range.

Two trapezoidal functions may be obtained by applying the FIR filter to each of the difference temperature distribution and the differentiated temperature distribution. Of these two trapezoidal functions, the one obtained by applying the FIR filter to the differentiated temperature distribution may indicate subtler changes, and therefore the abnormality range may be set in a finer manner. However, it is difficult to set a uniform temperature difference range in a graph obtained by applying the FIR filter to the differentiated temperature distribution if there are abnormality ranges lying adjacent to each other. Since the abnormality ranges set by the two trapezoidal functions differ from each other by about 1 m, using one of them will not make a large difference.

In this example, the result obtained by applying the FIR filter to the difference temperature is used to set the abnormality range. When the abnormality range is such a range that the value of the trapezoidal function is greater than 1, the abnormality range is a range of 684 m to 693 m. The signal processing region C is then set to 680 m to 697 m by taking into consideration the influence of the transfer function in FIG. 4 (±4 m).

The range indicated by m in the equation (6) mentioned above corresponds to this abnormality range. Here, the correction is performed based on the correlation mentioned above. Then, in the case of the non-negative constraint, the super-resolution signal processing is performed by using a condition that the temperature within the abnormality range is equal to or higher than a reference temperature and, at each correction, replacing any data which does not meet this condition.

Figure 23:
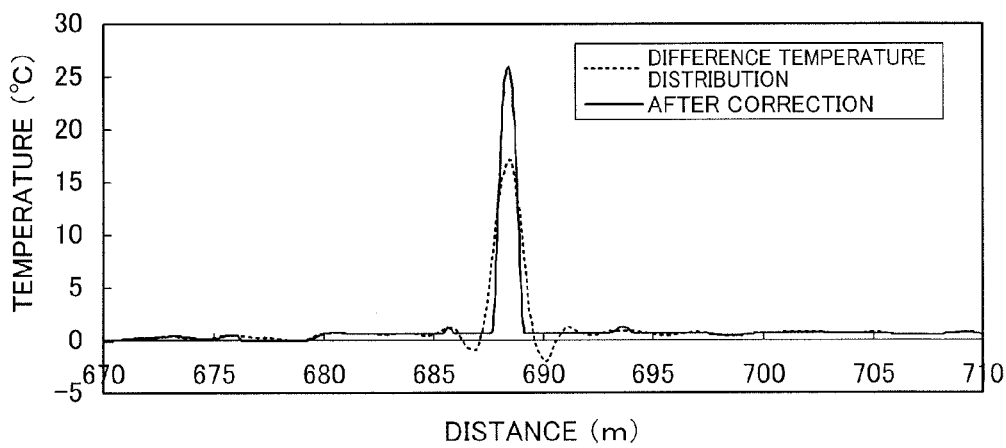
FIG. 23 is a graph illustrating the difference temperature distribution and the result of performing the super-resolution signal processing on the difference temperature distribution.

FIG. 23 illustrates a result thus obtained. FIG. 23 indicates that the super-resolution signal processing has increased the highest difference temperature by approximately 1.55 times (+9° C.). FIG. 23 also indicates that the non-negative constraint is working as a condition that the corrected temperature is equal to or higher than the difference temperature in a range of 680 m to 697 m.

According to a sensitivity coefficient which may be found from FIG. 13, the difference temperature is compressed by approximately 0.63 times when the heating length is 80 cm. Since the highest difference temperature before the correction is 16.3° C., a probable difference temperature is 25.9° C. (=16.3÷0.63). Since the highest difference temperature after the correction is 25.3° C., reliable correction is considered to have been done to such an extent that the error is reduced to 0.6° C.

Here, assume that a threshold to determine the presence of abnormality is set at 20° C. and the intervals of the data collection are two minutes. Then, if this embodiment is not employed, an alert will be put out at least two minutes after when the alert is put out in the embodiment. This may result in a large difference in a situation where abnormality is desired to be detected at an early stage.

In this embodiment, the difference temperature value is recovered by using the super-resolution signal processing which is an iterative technique using the transfer function under the constraint condition such as the non-negative constraint and the non-positive constraint. However, as long as the constraint condition is provided, it is possible to use a method of recovering the difference temperature value which combines blind deconvolution and a Fourier iterative algorithm, for example, instead of using the transfer function.

The applicability of the technique disclosed above will be described below.

Figure 24A:
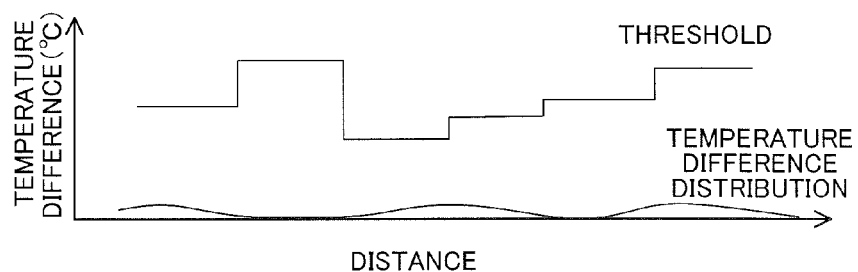
FIGS. 24A and 24B are views illustrating applicability 1 (part 1)
Figure 24B:
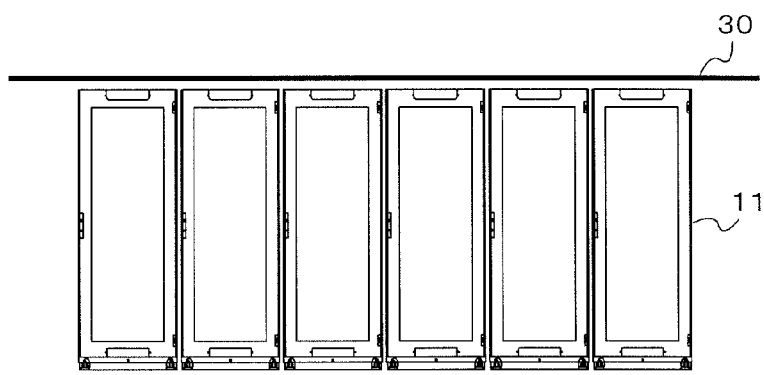

(Applicability 1) FIGS. 24A and 24B illustrate an example of application to a system configured to detect abnormality in how an optical fiber is laid over server racks of a data center to manage air conditioning.

In the case where an optical fiber is laid in a data center as illustrated in FIG. 2, it is possible to accurately detect the temperature distribution of the optical fiber in the length direction by using the method described in the prelude. However, it is difficult to apply the method described in the prelude to cases where it is difficult to lay an optical fiber inside racks, or a computer room is not divided into an equipment installation area and a free access floor.

Then, an optical fiber 30 is laid over racks 11 as illustrated in FIG. 24B. Moreover, the temperature inside each rack 11 during normal operation and the temperature distribution of the optical fiber 30 during that state are measured in advance, and a threshold for putting out an alert is set for each rack 11. FIG. 24A illustrates an alert threshold set for each rack 11 and a temperature difference distribution.

Figure 25A:
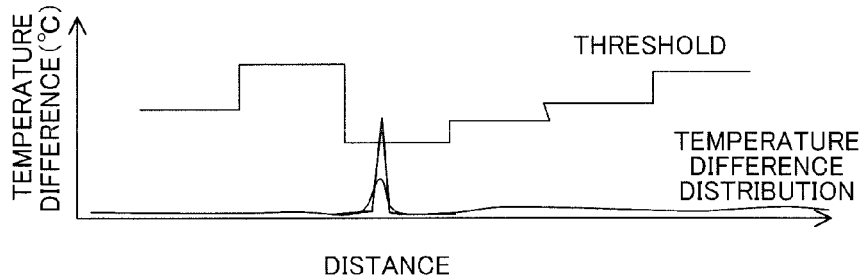
FIGS. 25A and 25B are views illustrating applicability 1 (part 2)
Figure 25B:
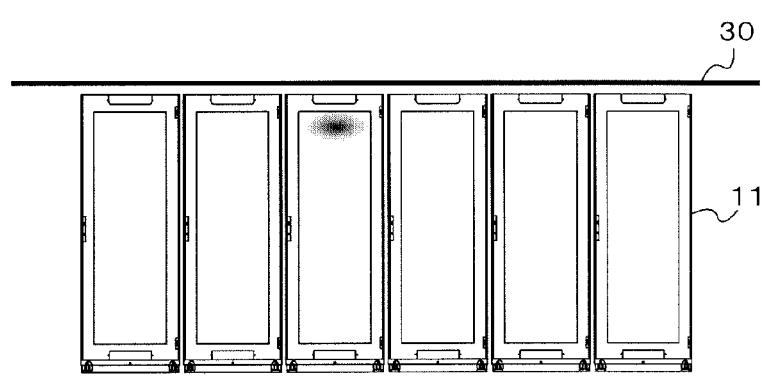

When abnormality occurs in one of the racks 11 as illustrated in FIG. 25B, for example, a peak appears on the temperature difference distribution at the location of the corresponding rack 11 as illustrated in FIG. 25A. By correcting this temperature difference distribution by using the method described in the embodiment, it is possible to accurately find the difference temperature, and therefore detect the present of abnormality at an early stage.

(Applicability 2) FIGS. 26A to 26D illustrate an example where the temperature measurement system described in the embodiment is applied to the detection of abnormality at a connected portion of pipes in a facility such as a chemical plant.

Figure 26A:
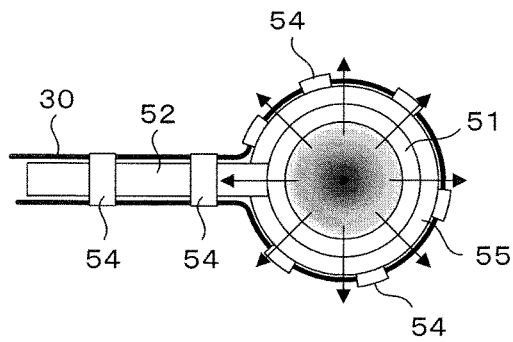
FIGS. 26A to 26D are views illustrating applicability 2.

Assume that while the plant is operated, high-temperature liquid or gas flows inside a main pipe 51, as illustrated in FIG. 26A. In this case, the pipe 51 expands when the plant is operated, and the pipe 51 shrinks when the plant is stopped.

Note that in FIGS. 26A to 26D, reference numeral 54 denotes pieces of tape fixing an optical fiber 30, and reference numeral 55 denotes a heat insulation material and a protection pipe disposed around the main pipe 51.

Figure 26B:
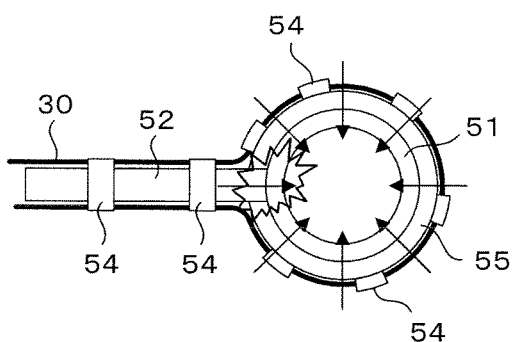
Figure 26C:
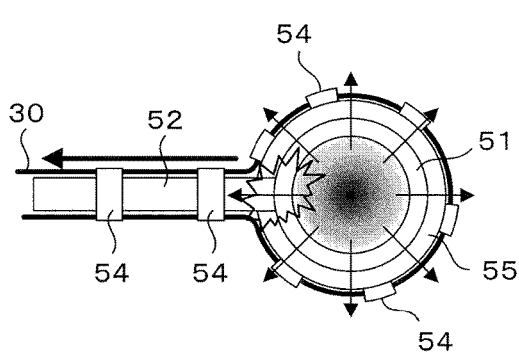
Figure 26D:
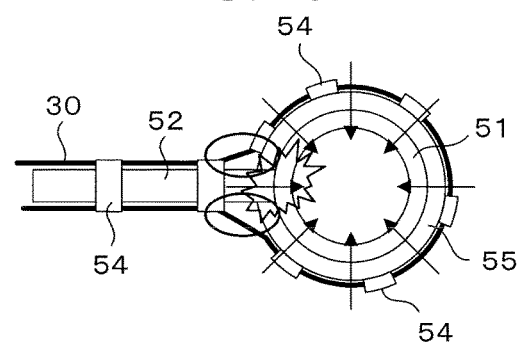

Metal fatigue occurs at a welded portion of the main pipe 51 and a branch pipe 52 as illustrated in FIG. 26B when the plant is stopped, for example. In this case, the next time the plant is run, the branch pipe 52 is pushed farther outwardly than usual as illustrated in FIG. 26C. When the plant then shifts to the stopped state, the branch pipe 52 thus pushed does not fully return and a crack is developed as illustrated in FIG. 26D.

In this state, the high-pressure liquid or gas that is left inside jets to the outside, thereby causing a partial temperature change. The temperature measurement system of the embodiment detects this partial temperature change and puts out an alert.

By detecting abnormality at a connected portion of pipes in a plant or the like as described above, a serious accident is prevented from occurring.

Figure 27:
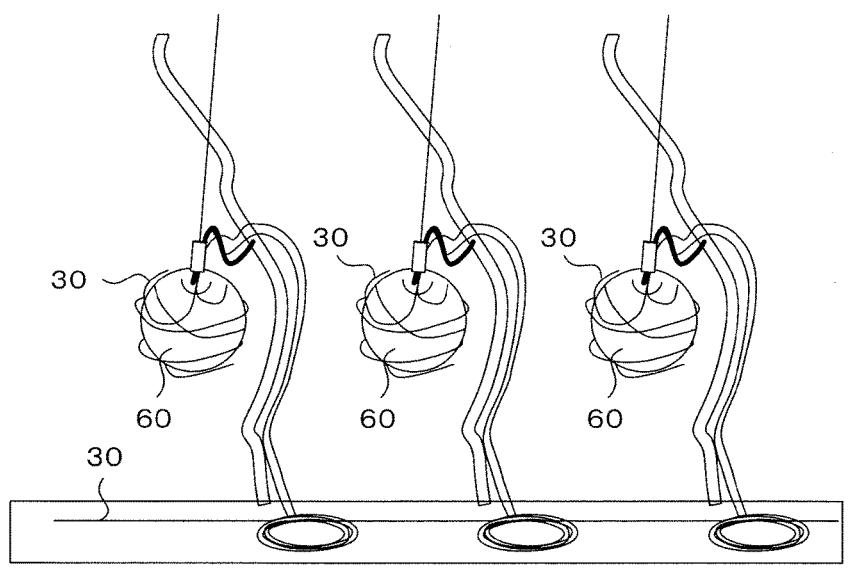
FIG. 27 is a view illustrating applicability 3.

(Applicability 3) FIG. 27 illustrates an example where the temperature measurement system described in the embodiment is applied to the growing of expensive fruits in a greenhouse and to the protection against theft thereof.

In this example, assume that, for the growing of Crown Melon in a greenhouse, a temperature distribution measurement apparatus (DTS) is used to measure the temperature of the soil, the temperature of the ambient air, and the temperature of the fruit, and the temperature of the inside of the greenhouse is managed based on these measurement results. Moreover, in this example, assume that the temperature distribution measurement apparatus is connected to a data processing apparatus to be used for abnormality detection as well.

When a thief steals a melon 60, for example, the thief tries to unwind an optical fiber 30 wound around the melon 60.

By acting carefully, the thief may avoid cutting the optical fiber 30. However, a subtle partial temperature change inevitably occurs when the thief tries to unwind the optical fiber 30. Thus, the temperature measurement system may detect the abnormality.

Upon detection of the abnormality, the temperature measurement system turns on an alarm lamp or actuates an alarm buzzer as well as notifies the occurrence of the abnormality to the manager. In this way, it is possible to prevent immense damage.

All examples and conditional language recited herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A temperature measurement system comprising:
    an optical fiber;
    a temperature distribution measurement apparatus configured to detect backscattered light by causing light to enter the optical fiber, and acquire a temperature distribution of the optical fiber in a length direction of the optical fiber based on a result of the detection; and
    a data processing apparatus configured to store the temperature distribution acquired by the temperature distribution measurement apparatus in the data processing apparatus, perform signal processing on a difference temperature distribution obtained by computing a difference between a current temperature distribution and a past temperature distribution, and determine whether or not abnormality is present based on a result of the signal processing, wherein
    when determining that abnormality is present based on the result of the signal processing, the data processing apparatus sets an abnormality region and reference temperature regions before and after the abnormality region along the length direction of the optical fiber, the abnormality region being a region where abnormality is considered to have occurred based on the result of the signal processing, the reference temperature regions being regions where no abnormality is considered to have occurred based on the result of the signal processing, and
    the data processing apparatus then performs signal processing which corrects a peak value in the abnormality region by using a temperature difference between the current temperature distribution and the past temperature distribution in the reference temperature regions as a reference.

2. The temperature measurement system according to claim 1, wherein when performing the signal processing which corrects the peak value, the data processing apparatus uses a non-negative constraint condition or a non-positive constraint condition derived from a result of integration of the difference temperature distribution.

3. The temperature measurement system according to claim 2, wherein the data processing apparatus puts out an alert when a peak value of the difference temperature distribution obtained by the correction by the signal processing which corrects the peak value exceeds a preset threshold.

4. The temperature measurement system according to claim 1, wherein the data processing apparatus determines whether or not abnormality is present by taking into consideration normal periodic temperature change.

5. The temperature measurement system according to claim 1, wherein the signal processing includes:
    performing a differentiation process on the difference temperature distribution.

6. The temperature measurement system according to claim 1, wherein the signal processing includes:
    acquiring a differentiated temperature distribution by performing a differentiation process on the difference temperature distribution, and
    applying an FIR (Finite Impulse Response) filter to the differentiated temperature distribution.

7. The temperature measurement system according to claim 2, wherein the signal processing which corrects the peak value is super-resolution signal processing including
    correcting the difference temperature distribution sequentially a plurality of times such that a squared error between convolution of the difference temperature distribution and a transfer function, and the difference temperature distribution decreases at each correction, and
    each time the correction is performed, replacing difference temperatures in the reference temperature regions after the correction with an estimated difference temperature such that the constraint condition is met.

8. The temperature measurement system according to claim 1, wherein data on the past temperature distribution is a sum of weighted pieces of data on a plurality of past temperature distributions.

9. The temperature measurement system according to claim 1, wherein the optical fiber is laid along a pipe.

10. The temperature measurement system according to claim 1, wherein the optical fiber is laid along electronic equipment.

11. The temperature measurement system according to claim 1, wherein the optical fiber is laid around a plant.

12. An abnormality detection method comprising:
    by using a temperature distribution measurement apparatus, acquiring backscattered light by causing light to enter an optical fiber from one end of the optical fiber; and
    by using a data processing apparatus, storing an intensity distribution of the backscattered light acquired by the temperature distribution measurement apparatus in the data processing apparatus, performing signal processing on a difference temperature distribution obtained by computing a difference between a current temperature distribution and a past temperature distribution, and determining whether or not abnormality is present based on a result of the signal processing, wherein
    when determining that abnormality is present based on the result of the signal processing, the data processing apparatus sets an abnormality region and reference temperature regions before and after the abnormality region along a length direction of the optical fiber, the abnormality region being a region where abnormality is considered to have occurred based on the result of the signal processing, the reference temperature regions being regions where no abnormality is considered to have occurred based on the result of the signal processing, and the data processing apparatus then performs signal processing which corrects a peak value in the abnormality region by using a temperature difference between the current temperature distribution and the past temperature distribution in the reference temperature regions as a reference.

13. The abnormality detection method according to claim 12, wherein when performing the signal processing which corrects the peak value, the data processing apparatus uses a non-negative constraint condition or a non-positive constraint condition derived from a result of integration of the difference temperature distribution.

14. The abnormality detection method according to claim 13, wherein the data processing apparatus puts out an alert when a peak value of the difference temperature distribution obtained by the correction by the signal processing which corrects the peak value exceeds a preset threshold.

15. The abnormality detection method according to claim 12, wherein the signal processing includes:
performing a differentiation process on the difference temperature distribution.

16. The abnormality detection method according to claim 12, wherein the signal processing includes:
acquiring a differentiated temperature distribution by performing a differentiation process on the difference temperature distribution, and
applying an FIR (Finite Impulse Response) filter to the differentiated temperature distribution.

17. The abnormality detection method according to claim 13, wherein the signal processing which corrects the peak value is super-resolution signal processing including
correcting the difference temperature distribution sequentially a plurality of times such that a squared error between convolution of the difference temperature distribution and a transfer function, and the difference temperature distribution decreases at each correction, and
each time the correction is performed, replacing difference temperatures in the reference temperature regions after the correction with an estimated difference temperature such that the constraint condition is met.

18. The abnormality detection method according to claim 12, wherein data on the past temperature distribution is a sum of weighted pieces of data on a plurality of past temperature distributions.

* * * * *